United States Patent
Bridges

(10) Patent No.: US 9,075,025 B2
(45) Date of Patent: Jul. 7, 2015

(54) APPARATUS AND METHOD TO COMPENSATE BEARING RUNOUT IN LASER TRACKER

(71) Applicant: FARO Technologies, Inc., Lake Mary, FL (US)

(72) Inventor: Robert E. Bridges, Kennett Square, PA (US)

(73) Assignee: FARO TECHNOLOGIES, INC., Lake Mary, FL (US)

( * ) Notice: Subject to any disclaimer, the term of this patent is extended or adjusted under 35 U.S.C. 154(b) by 130 days.

(21) Appl. No.: 13/888,442

(22) Filed: May 7, 2013

(65) Prior Publication Data

US 2013/0308117 A1  Nov. 21, 2013

Related U.S. Application Data

(60) Provisional application No. 61/647,697, filed on May 16, 2012.

(51) Int. Cl.
| | |
|---|---|
| *G01C 3/08* | (2006.01) |
| *G01N 21/93* | (2006.01) |
| *G01B 21/04* | (2006.01) |
| *G01C 15/00* | (2006.01) |
| *G01M 13/04* | (2006.01) |
| *G01S 17/66* | (2006.01) |
| *G01S 7/497* | (2006.01) |

(52) U.S. Cl.
CPC .............. *G01N 21/93* (2013.01); *G01B 21/045* (2013.01); *G01C 15/002* (2013.01); *G01M 13/04* (2013.01); *G01S 17/66* (2013.01); *G01S 7/4972* (2013.01)

(58) Field of Classification Search
CPC ........... G01S 11/12; G01S 17/46; G01C 3/00; C30B 15/14; C30B 15/26
USPC ................................................. 356/3.09, 3.02
See application file for complete search history.

(56) References Cited

U.S. PATENT DOCUMENTS

| | | |
|---|---|---|
| 6,138,367 A | 10/2000 | Raby |
| 6,243,658 B1 | 6/2001 | Raby |

(Continued)

FOREIGN PATENT DOCUMENTS

| | | |
|---|---|---|
| EP | 1750085 | 2/2007 |
| WO | 2005026772 | 3/2005 |

(Continued)

OTHER PUBLICATIONS

Muralikrishnan, et al., "ASME B89.4.19 Performance Evaluation Tests and Geometric Misalignments in Laser Trackers," J. Res. Natl. Inst. Stand. Technol. 114, 21-35 (2009).

(Continued)

*Primary Examiner* — Isam Alsomiri
*Assistant Examiner* — Samantha K Abraham
(74) *Attorney, Agent, or Firm* — Cantor Colburn LLP

(57) ABSTRACT

An apparatus and method for correcting errors in measurement of three-dimensional coordinates of a retroreflector by a coordinate measurement device is provided. The method includes measuring a plurality of first angles, a plurality of first and second displacements along an axis, sending a beam of light to the retroreflector target, measuring two angles and a distance to the retroreflector, and determining the three-dimensional coordinates of the retroreflector.

16 Claims, 21 Drawing Sheets

(56) References Cited

U.S. PATENT DOCUMENTS

| | | | |
|---|---|---|---|
| 7,701,559 | B2 | 4/2010 | Bridges et al. |
| 7,800,758 | B1 | 9/2010 | Bridges et al. |
| 2005/0212513 | A1* | 9/2005 | Yamashita et al. ....... 324/207.25 |
| 2005/0225769 | A1* | 10/2005 | Bankhead et al. ............ 356/497 |
| 2010/0128259 | A1 | 5/2010 | Bridges et al. |
| 2012/0206716 | A1 | 8/2012 | Cramer et al. |
| 2012/0326709 | A1 | 12/2012 | Westermark et al. |

FOREIGN PATENT DOCUMENTS

| | | |
|---|---|---|
| WO | 2010057169 | 5/2010 |
| WO | 2013092319 A1 | 6/2013 |

OTHER PUBLICATIONS

E.R. Marsh "Precision Spindle Metrology" (109 pages) ASPE Annuyal Meeting.

International Search Report mailed Jul. 29, 2013 for International Application Serial No. PCT/US2013/039799; International filing date May 7, 2013.

Marsh et al "Precision Spindle Metrology: Test Instrumentation" Chapter 3-5 cover and front page (pp. 39-128) Jan. 1, 2010, Destech Publications, US; ISN: 978-1-61344-582-2; retrieved from the internet URL:http://www.knovel.com/web/portal/browse/display?_EXT_KNOVEL_DISPLAY_bookid=4588.

Written Opinion of the International Searching Authority mailed Jul. 29, 2013 for International Application Serial No. PCT/US2013/039799; International filing date May 7, 2013.

\* cited by examiner

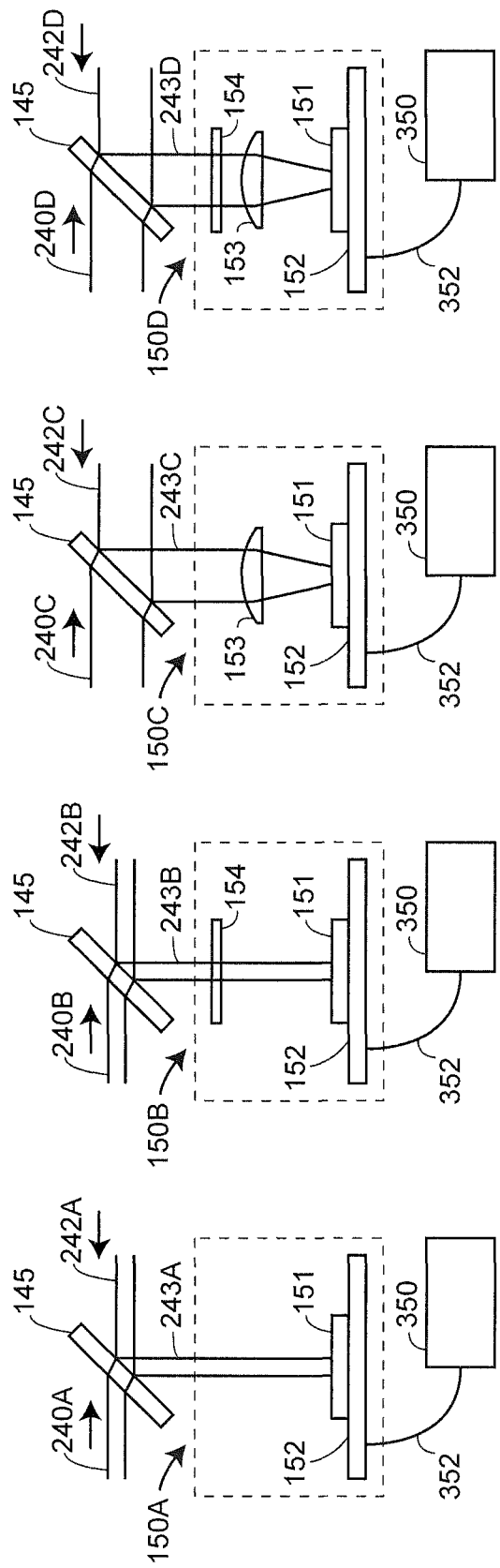

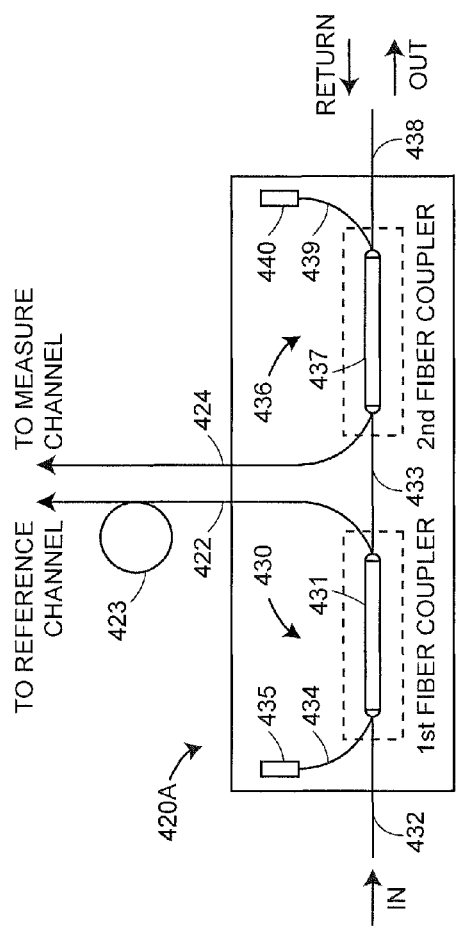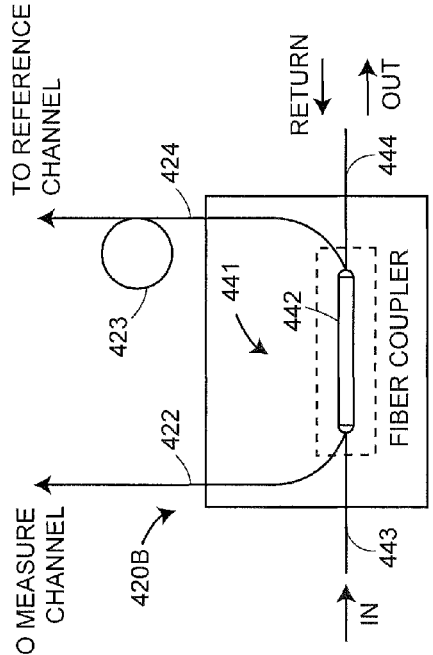
PRIOR ART
FIGURE 8A
PRIOR ART
FIGURE 8B

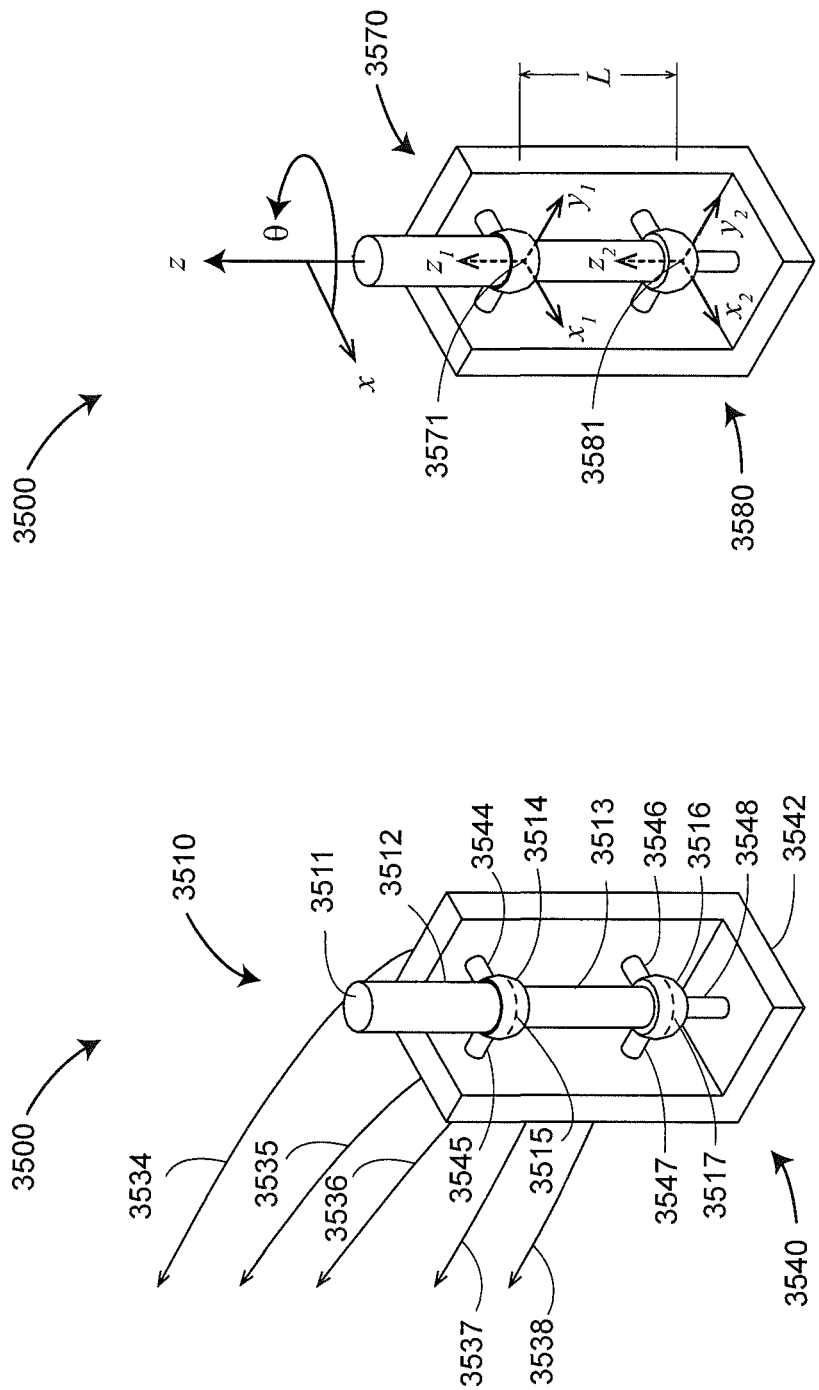

APPARATUS AND METHOD TO COMPENSATE BEARING RUNOUT IN LASER TRACKER

CROSS REFERENCE TO RELATED APPLICATIONS

The present application claims the benefit of and is a nonprovisional of U.S. Provisional Application Ser. No. 61/647,697 filed on May 16, 2012, the contents of which are incorporated by reference herein in its entirety.

BACKGROUND

The present disclosure relates to a coordinate measuring device. One set of coordinate measurement devices belongs to a class of instruments that measure the three-dimensional (3D) coordinates of a point by sending a laser beam to the point. The laser beam may impinge directly on the point or on a retroreflector target in contact with the point. In either case, the instrument determines the coordinates of the point by measuring the distance and the two angles to the target. The distance is measured with a distance-measuring device such as an absolute distance meter or an interferometer. The angles are measured with an angle-measuring device such as an angular encoder. A gimbaled beam-steering mechanism within the instrument directs the laser beam to the point of interest.

The laser tracker is a particular type of coordinate-measuring device that tracks the retroreflector target with one or more laser beams it emits. Coordinate-measuring devices closely related to the laser tracker are the laser scanner and the total station. The laser scanner steps one or more laser beams to points on a surface. It picks up light scattered from the surface and from this light determines the distance and two angles to each point. The total station, which is most often used in surveying applications, may be used to measure the coordinates of diffusely scattering or retroreflective targets. Hereinafter, the term laser tracker is used in a broad sense to include laser scanners and total stations.

Ordinarily the laser tracker sends a laser beam to a retroreflector target. A common type of retroreflector target is the spherically mounted retroreflector (SMR), which comprises a cube-corner retroreflector embedded within a metal sphere. The cube-corner retroreflector comprises three mutually perpendicular mirrors. The vertex, which is the common point of intersection of the three mirrors, is located at the center of the sphere. Because of this placement of the cube corner within the sphere, the perpendicular distance from the vertex to any surface on which the SMR rests remains constant, even as the SMR is rotated. Consequently, the laser tracker can measure the 3D coordinates of a surface by following the position of an SMR as it is moved over the surface. Stating this another way, the laser tracker needs to measure only three degrees of freedom (one radial distance and two angles) to fully characterize the 3D coordinates of a surface.

One type of laser tracker contains only an interferometer (IFM) without an absolute distance meter (ADM). If an object blocks the path of the laser beam from one of these trackers, the IFM loses its distance reference. The operator must then track the retroreflector to a known location to reset to a reference distance before continuing the measurement. A way around this limitation is to put an ADM in the tracker. The ADM can measure distance in a point-and-shoot manner, as described in more detail below. Some laser trackers contain only an ADM without an interferometer. U.S. Pat. No. 7,352,446 ('446) to Bridges et al., the contents of which are herein incorporated by reference, describes a laser tracker having only an ADM (and no IFM) that is able to accurately scan a moving target. Prior to the '446 patent, absolute distance meters were too slow to accurately find the position of a moving target.

A gimbal mechanism within the laser tracker may be used to direct a laser beam from the tracker to the SMR. Part of the light retroreflected by the SMR enters the laser tracker and passes onto a position detector. A control system within the laser tracker can use the position of the light on the position detector to adjust the rotation angles of the mechanical axes of the laser tracker to keep the laser beam centered on the SMR. In this way, the tracker is able to follow (track) an SMR that is moved over the surface of an object of interest.

Angle measuring devices such as angular encoders are attached to the mechanical axes of the tracker. The one distance measurement and two angle measurements performed by the laser tracker are sufficient to completely specify the three-dimensional location of the SMR.

Several laser trackers are available or have been proposed for measuring six, rather than the ordinary three, degrees of freedom. Exemplary six degree-of-freedom (six-DOF) systems are described by U.S. Pat. No. 7,800,758 ('758) to Bridges et al., the contents of which are herein incorporated by reference, and U.S. Published Patent Application No. 2010/0128259 to Bridges et al., the contents of which are herein incorporated by reference.

Compensation parameters are numerical values stored in software or firmware accessible to the tracker. These numerical values are applied to raw tracker data to improve tracker accuracy. The manufacturer and, in some cases, the user of the tracker find the compensation parameters by performing measurements called compensation procedures. Today laser trackers use compensation parameters to account for mechanical errors such as axis non-squareness and axis offset along with optomechanical errors such as laser beam offset and beam angle deviation with respect to a tracker gimbal point. However, in present generation laser trackers, compensation parameters that account for the effects of bearing runout are not included. Such effects can be relatively large. Furthermore, bearing runout can degrade the accuracy of compensation of angular encoders. Procedures are needed that enable the collecting and application of compensation parameters to minimize the errors resulting from bearing runout.

SUMMARY

According to an embodiment, there is provided a method for correcting errors in measurement of three-dimensional coordinates of a retroreflector target by a coordinate measurement device, the coordinate measurement device configured to send a first beam of light to the retroreflector target, the retroreflector target configured to return a portion of the first beam as a second beam, the method comprising steps of: providing the coordinate measurement device with a first axle, a second axle, a first motor, a second motor, a first angle measuring device, a second angle measuring device, a distance meter, and a processor, the first axle configured to rotate about a first axis, the first axle supported by a first bearing and a second bearing, the first motor configured to rotate the first axle about the first axis by a first angle, the first angle measuring device configured to measure the first angle, the second axle configured to rotate about a second axis, the second axle supported by a third bearing and a fourth bearing, the second motor configured to rotate the second axle about the second axis by a second angle, the second angle measuring device configured to measure the second angle, the distance meter configured to measure a first distance from the coordinate measurement device to the retroreflector target based at least in part on a first portion of the second beam received by a first optical detector; measuring a plurality of first angles with the first angle measuring device; measuring a plurality of first displacements at a first position along the first axis, each of the plurality of first displacements associated with one of the plurality of first angles, the first displacements taken along a first line perpendicular to the first axis; measuring a plurality of second displacements at a second position along the first axis, each of the plurality of second displacements associated with one of the plurality of first angles, the second displacements taken along a second line perpendicular to the first axis, there being a first separation distance between the first line and the second line; determining compensation values based at least in part on the plurality of first angles, the plurality of first displacements, the plurality of second displacements, and the first separation distance; sending the first beam to the retroreflector target; measuring a first retroreflector angle with the first angle measuring device; measuring a second retroreflector angle with the second angle measuring device; measuring the first distance with the distance meter; calculating three-dimensional coordinates of the retroreflector target based at least in part on the first retroreflector angle, the second retroreflector angle, the first distance, and the compensation values; and storing the three-dimensional coordinates of the retroreflector target in memory.

According to an embodiment, there is provided a coordinate measurement device for measuring three-dimensional coordinates of a retroreflector target, the coordinate measurement device configured to send a first beam of light to the retroreflector target, the retroreflector target configured to return a portion of the first beam as a second beam, the device comprising a first axle, a second axle, a first motor, a second motor, a first angle measuring device, a second angle measuring device, a distance meter, a rotation counter, and a processor, the first axle configured to rotate about a first axis, the first axle supported by a first bearing and a second bearing, the first motor configured to rotate the first axle about the first axis by a first angle, the first angle measuring device configured to measure the first angle, the second axle configured to rotate about a second axis, the second axle supported by a third bearing and a fourth bearing, the second motor configured to rotate the second axle about the second axis by a second angle, the second angle measuring device configured to measure the second angle, the distance meter configured to measure a first distance from the coordinate measurement device to the retroreflector target based at least in part on a first portion of the second beam received by a first optical detector, the rotation counter configured to measure a number of rotations of the first axle.

BRIEF DESCRIPTION OF THE DRAWINGS

Referring now to the drawings, exemplary embodiments are shown which should not be construed to be limiting regarding the entire scope of the disclosure, and wherein the elements are numbered alike in several FIGURES:

FIGS. 4A and 4B, shows two types of prior art afocal beam expanders;

FIGS. 6A-D are schematic figures that show four types of prior art position detector assemblies;

FIGS. 8A and 8B are schematic figures showing fiber-optic elements within a prior art fiber-optic network;

FIGS. 15A and 15B are perspective views of prior art apparatus that measure bearing errors;

DETAILED DESCRIPTION

Figure 1:
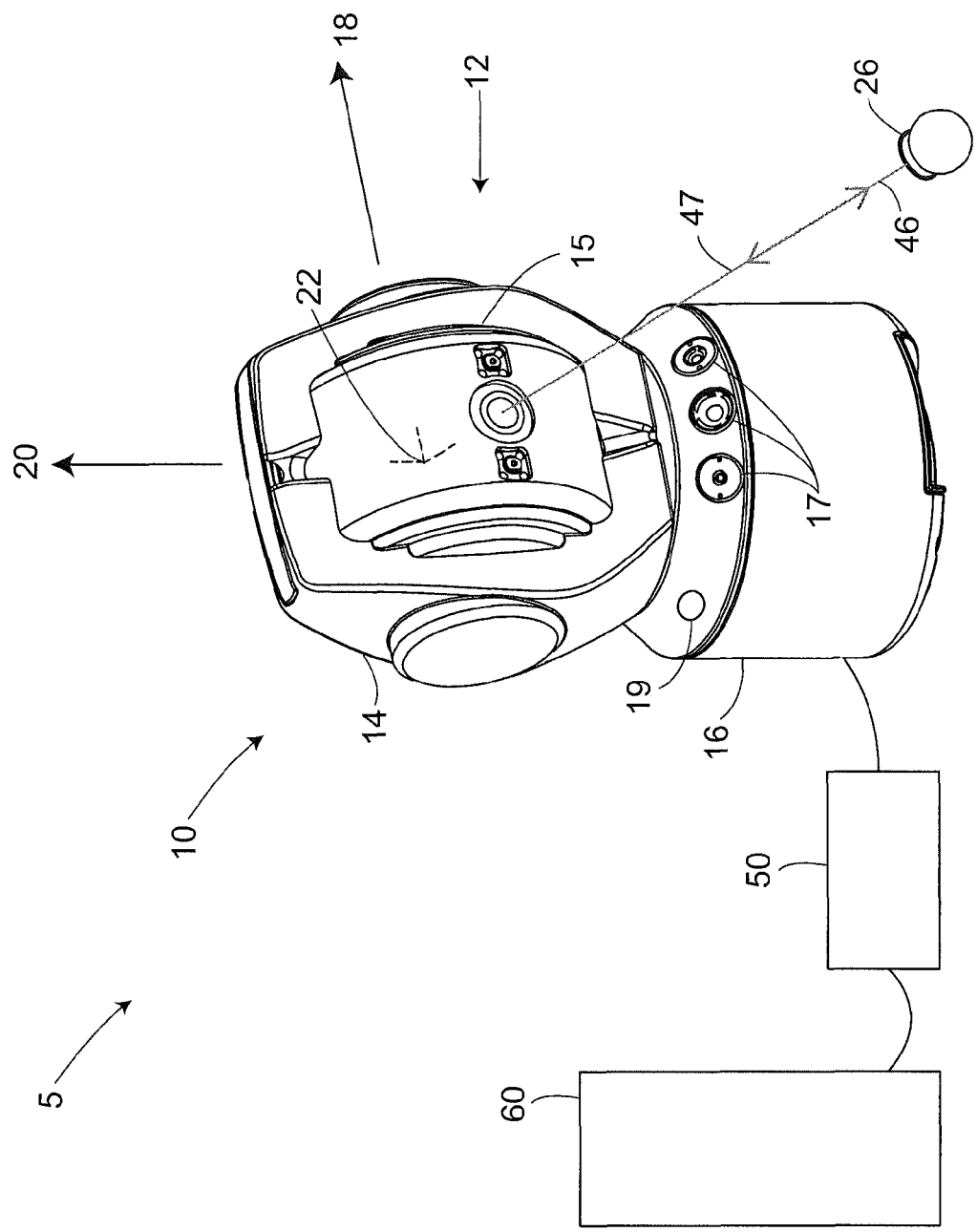
FIG. 1 is a perspective view of a laser tracker system with a retroreflector target in accordance with an embodiment of the present invention.

An exemplary laser tracker system 5 illustrated in FIG. 1 includes a laser tracker 10, a retroreflector target 26, an optional auxiliary unit processor 50, and an optional auxiliary computer 60. An exemplary gimbaled beam-steering mechanism 12 of laser tracker 10 comprises a zenith carriage 14 mounted on an azimuth base 16 and rotated about an azimuth axis 20. A payload 15 is mounted on the zenith carriage 14 and rotated about a zenith axis 18. Zenith axis 18 and azimuth axis 20 intersect orthogonally, internally to tracker 10, at gimbal point 22, which is typically the origin for distance measurements. A laser beam 46 virtually passes through the gimbal point 22 and is pointed orthogonal to zenith axis 18. In other words, laser beam 46 lies in a plane approximately perpendicular to the zenith axis 18 and that passes through the azimuth axis 20. Outgoing laser beam 46 is pointed in the desired direction by rotation of payload 15 about zenith axis 18 and by rotation of zenith carriage 14 about azimuth axis 20. A zenith angular encoder, internal to the tracker, is attached to a zenith mechanical axis aligned to the zenith axis 18. An azimuth angular encoder, internal to the tracker, is attached to an azimuth mechanical axis aligned to the azimuth axis 20. The zenith and azimuth angular encoders measure the zenith and azimuth angles of rotation to relatively high accuracy. Outgoing laser beam 46 travels to the retroreflector target 26, which might be, for example, a spherically mounted retroreflector (SMR) as described above. By measuring the radial distance between gimbal point 22 and retroreflector 26, the rotation angle about the zenith axis 18, and the rotation angle about the azimuth axis 20, the position of retroreflector 26 is found within the spherical coordinate system of the tracker.

Outgoing laser beam 46 may include one or more laser wavelengths, as described hereinafter. For the sake of clarity and simplicity, a steering mechanism of the sort shown in FIG. 1 is assumed in the following discussion. However, other types of steering mechanisms are possible. For example, it is possible to reflect a laser beam off a mirror rotated about the azimuth and zenith axes. The techniques described herein are applicable, regardless of the type of steering mechanism.

Magnetic nests 17 may be included on the laser tracker for resetting the laser tracker to a "home" position for different sized SMRs—for example, 1.5, ⅞, and ½ inch SMRs. An on-tracker retroreflector 19 may be used to reset the tracker to a reference distance. In addition, an on-tracker mirror, not visible from the view of FIG. 1, may be used in combination with the on-tracker retroreflector to enable performance of a self-compensation, as described in U.S. Pat. No. 7,327,446, the contents of which are incorporated by reference herein.

Figure 2:
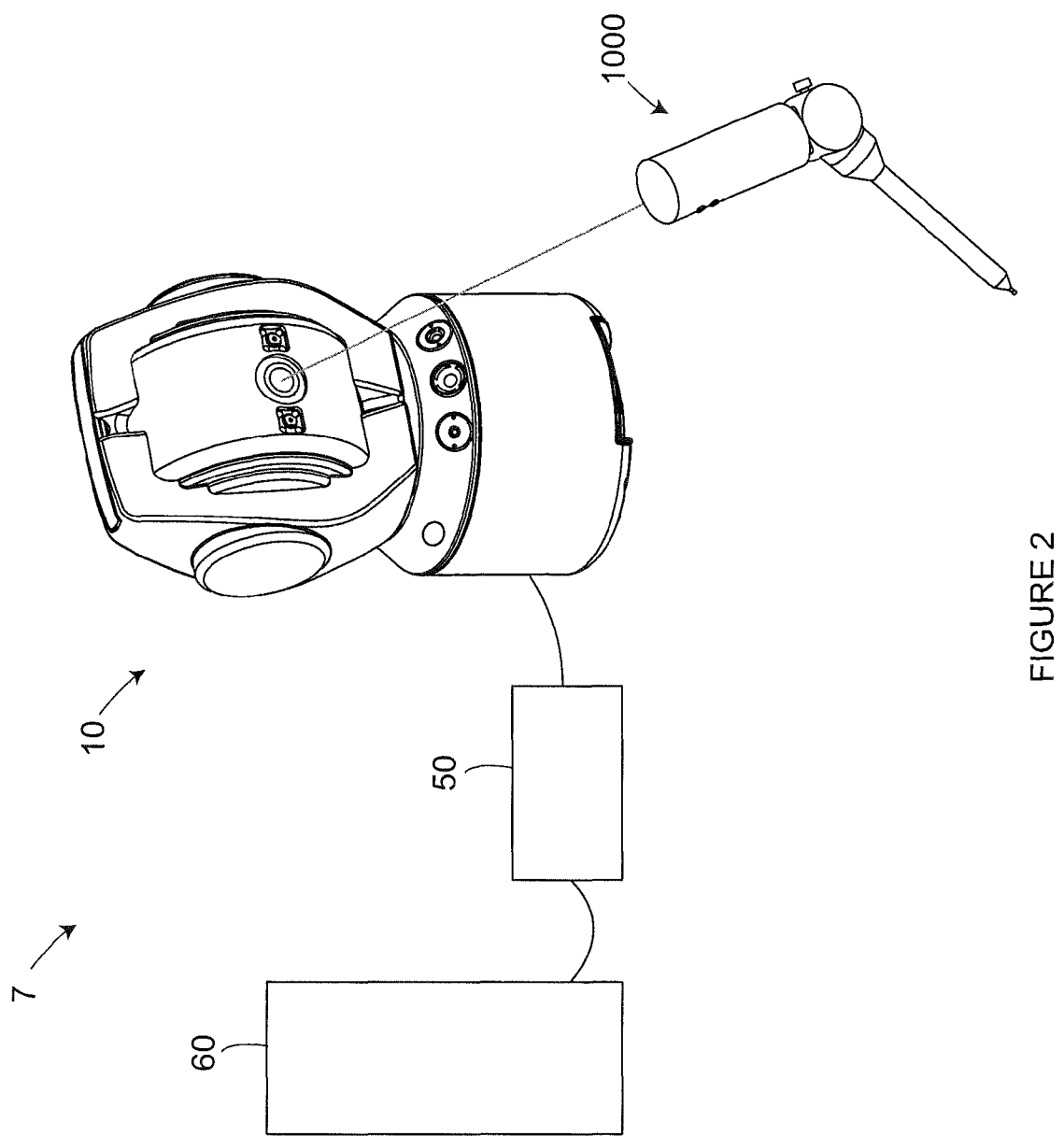
FIG. 2 is a perspective view of a laser tracker system with a six-DOF target in accordance with an embodiment of the present invention.

FIG. 2 shows an exemplary laser tracker system 7 that is like the laser tracker system 5 of FIG. 1 except that retroreflector target 26 is replaced with a six-DOF probe 1000. In FIG. 1, other types of retroreflector targets may be used. For example, a cateye retroreflector, which is a glass retroreflector in which light focuses to a small spot of light on a reflective rear surface of the glass structure, is sometimes used.

Figure 3:
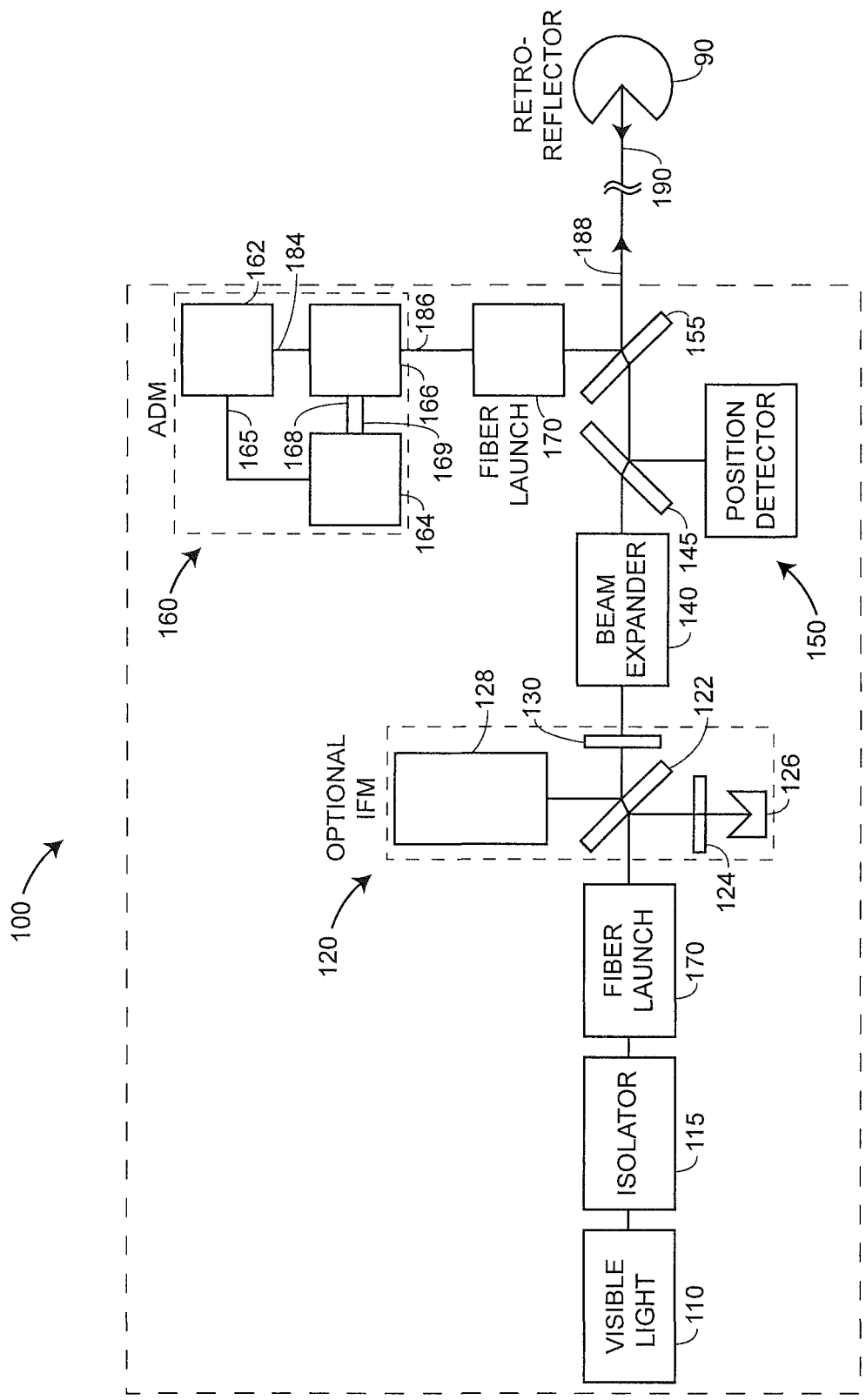
FIG. 3 is a block diagram describing elements of laser tracker optics and electronics in accordance with an embodiment of the present invention.

FIG. 3 is a block diagram showing optical and electrical elements in a laser tracker embodiment. It shows elements of a laser tracker that emit two wavelengths of light—a first wavelength for an ADM and a second wavelength for a visible pointer and for tracking. The visible pointer enables the user to see the position of the laser beam spot emitted by the tracker. The two different wavelengths are combined using a free-space beam splitter. Electrooptic (EO) system 100 includes visible light source 110, isolator 115, optional first fiber launch 170, optional interferometer (IFM) 120, beam expander 140, first beam splitter 145, position detector assembly 150, second beam splitter 155, ADM 160, and second fiber launch 170.

Visible light source 110 may be a laser, superluminescent diode, or other light emitting device. The isolator 115 may be a Faraday isolator, attenuator, or other device capable of reducing the light that reflects back into the light source. Optional IFM may be configured in a variety of ways. As a specific example of a possible implementation, the IFM may include a beam splitter 122, a retroreflector 126, quarter waveplates 124, 130, and a phase analyzer 128. The visible light source 110 may launch the light into free space, the light then traveling in free space through the isolator 115, and optional IFM 120. Alternatively, the isolator 115 may be coupled to the visible light source 110 by a fiber optic cable. In this case, the light from the isolator may be launched into free space through the first fiber-optic launch 170, as discussed herein below with reference to FIG. 5.

Figure 4:
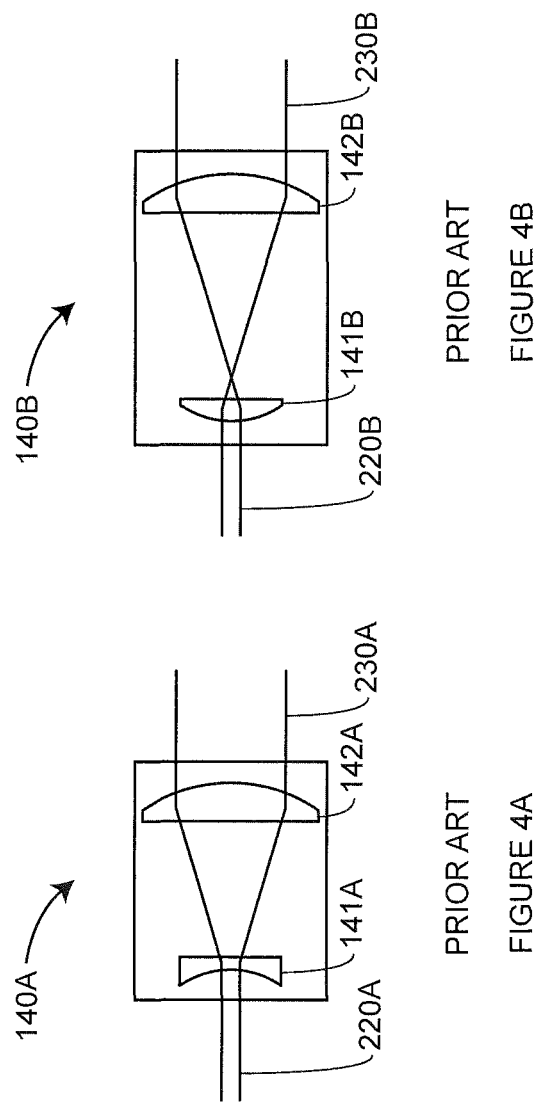
FIG. 4, which includes

Beam expander 140 may be set up using a variety of lens configurations, but two commonly used prior-art configurations are shown in FIGS. 4A and 4B. FIG. 4A shows a configuration 140A based on the use of a negative lens 141A and a positive lens 142A. A beam of collimated light 220A incident on the negative lens 141A emerges from the positive lens 142A as a larger beam of collimated light 230A. FIG. 4B shows a configuration 140B based on the use of two positive lenses 141B, 142B. A beam of collimated light 220B incident on a first positive lens 141B emerges from a second positive lens 142B as a larger beam of collimated light 230B. Of the light leaving the beam expander 140, a small amount reflects off the beam splitters 145, 155 on the way out of the tracker and is lost. That part of the light that passes through the beam splitter 155 is combined with light from the ADM 160 to form a composite beam of light 188 that leaves that laser tracker and travels to the retroreflector 90.

In an embodiment, the ADM 160 includes a light source 162, ADM electronics 164, a fiber network 166, an interconnecting electrical cable 165, and interconnecting optical fibers 168, 169, 184, 186. ADM electronics send electrical modulation and bias voltages to light source 162, which may, for example, be a distributed feedback laser that operates at a wavelength of approximately 1550 nm. In an embodiment, the fiber network 166 may be the prior art fiber-optic network 420A shown in FIG. 8A. In this embodiment, light from the light source 162 in FIG. 3 travels over the optical fiber 184, which is equivalent to the optical fiber 432 in FIG. 8A.

The fiber network of FIG. 8A includes a first fiber coupler 430, a second fiber coupler 436, and low-transmission reflectors 435, 440. The light travels through the first fiber coupler 430 and splits between two paths, the first path through optical fiber 433 to the second fiber coupler 436 and the second path through optical fiber 422 and fiber length equalizer 423. Fiber length equalizer 423 connects to fiber length 168 in FIG. 3, which travels to the reference channel of the ADM electronics 164. The purpose of fiber length equalizer 423 is to match the length of optical fibers traversed by light in the reference channel to the length of optical fibers traversed by light in the measure channel. Matching the fiber lengths in this way reduces ADM errors caused by changes in the ambient temperature. Such errors may arise because the effective optical path length of an optical fiber is equal to the average index of refraction of the optical fiber times the length of the fiber. Since the index of refraction of the optical fibers depends on the temperature of the fiber, a change in the temperature of the optical fibers causes changes in the effective optical path lengths of the measure and reference channels. If the effective optical path length of the optical fiber in the measure channel changes relative to the effective optical path length of the optical fiber in the reference channel, the result will be an apparent shift in the position of the retroreflector target 90, even if the retroreflector target 90 is kept stationary. To get around this problem, two steps are taken. First, the length of the fiber in the reference channel is matched, as nearly as possible, to the length of the fiber in the measure channel. Second, the measure and reference fibers are routed side by side to the extent possible to ensure that the optical fibers in the two channels see nearly the same changes in temperature.

The light travels through the second fiber optic coupler 436 and splits into two paths, the first path to the low-reflection fiber terminator 440 and the second path to optical fiber 438, from which it travels to optical fiber 186 in FIG. 3. The light on optical fiber 186 travels through to the second fiber launch 170.

Figure 5:
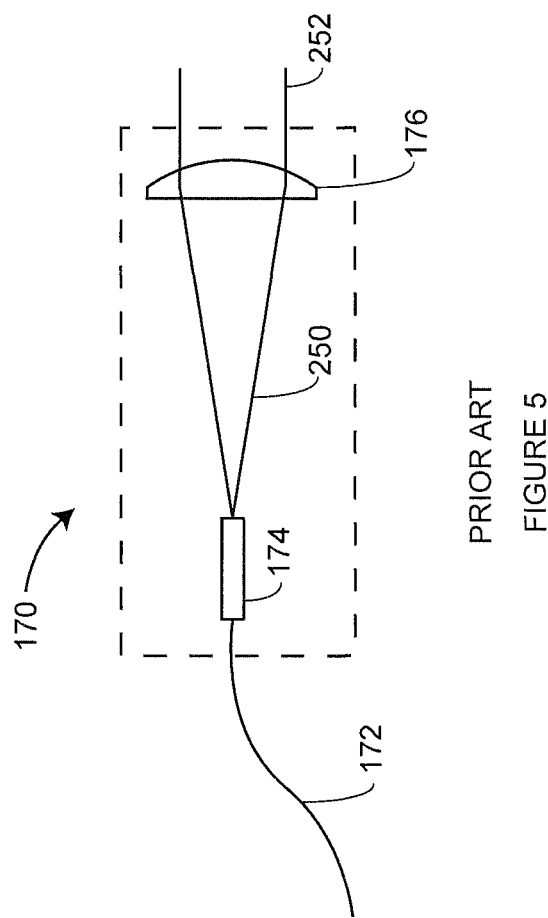
FIG. 5 shows a prior art fiber-optic beam launch.

In an embodiment, fiber launch 170 is shown in prior art FIG. 5. The light from optical fiber 186 of FIG. 3 goes to fiber 172 in FIG. 5. The fiber launch 170 includes optical fiber 172, ferrule 174, and lens 176. The optical fiber 172 is attached to ferrule 174, which is stably attached to a structure within the laser tracker 10. If desired, the end of the optical fiber may be polished at an angle to reduce back reflections. The light 250 emerges from the core of the fiber, which may be a single mode optical fiber with a diameter of between 4 and 12 micrometers, depending on the wavelength of the light being used and the particular type of optical fiber. The light 250 diverges at an angle and intercepts lens 176, which collimates it. The method of launching and receiving an optical signal through a single optical fiber in an ADM system was described in reference to FIG. 3 in patent '758.

Referring to FIG. 3, the beam splitter 155 may be a dichroic beam splitter, which transmits different wavelengths than it reflects. In an embodiment, the light from the ADM 160 reflects off dichroic beam splitter 155 and combines with the light from the visible laser 110, which is transmitted through the dichroic beam splitter 155. The composite beam of light 188 travels out of the laser tracker to retroreflector 90 as a first beam, which returns a portion of the light as a second beam. That portion of the second beam that is at the ADM wavelength reflects off the dichroic beam splitter 155 and returns to the second fiber launch 170, which couples the light back into the optical fiber 186.

In an embodiment, the optical fiber 186 corresponds to the optical fiber 438 in FIG. 8A. The returning light travels from optical fiber 438 through the second fiber coupler 436 and splits between two paths. A first path leads to optical fiber 424 that, in an embodiment, corresponds to optical fiber 169 that leads to the measure channel of the ADM electronics 164 in FIG. 3. A second path leads to optical fiber 433 and then to the first fiber coupler 430. The light leaving the first fiber coupler 430 splits between two paths, a first path to the optical fiber 432 and a second path to the low reflectance termination 435. In an embodiment, optical fiber 432 corresponds to the optical fiber 184, which leads to the light source 162 in FIG. 3. In most cases, the light source 162 contains a built-in Faraday isolator that minimizes the amount of light that enters the light source from optical fiber 432. Excessive light fed into a laser in the reverse direction can destabilize the laser.

Figure 7:
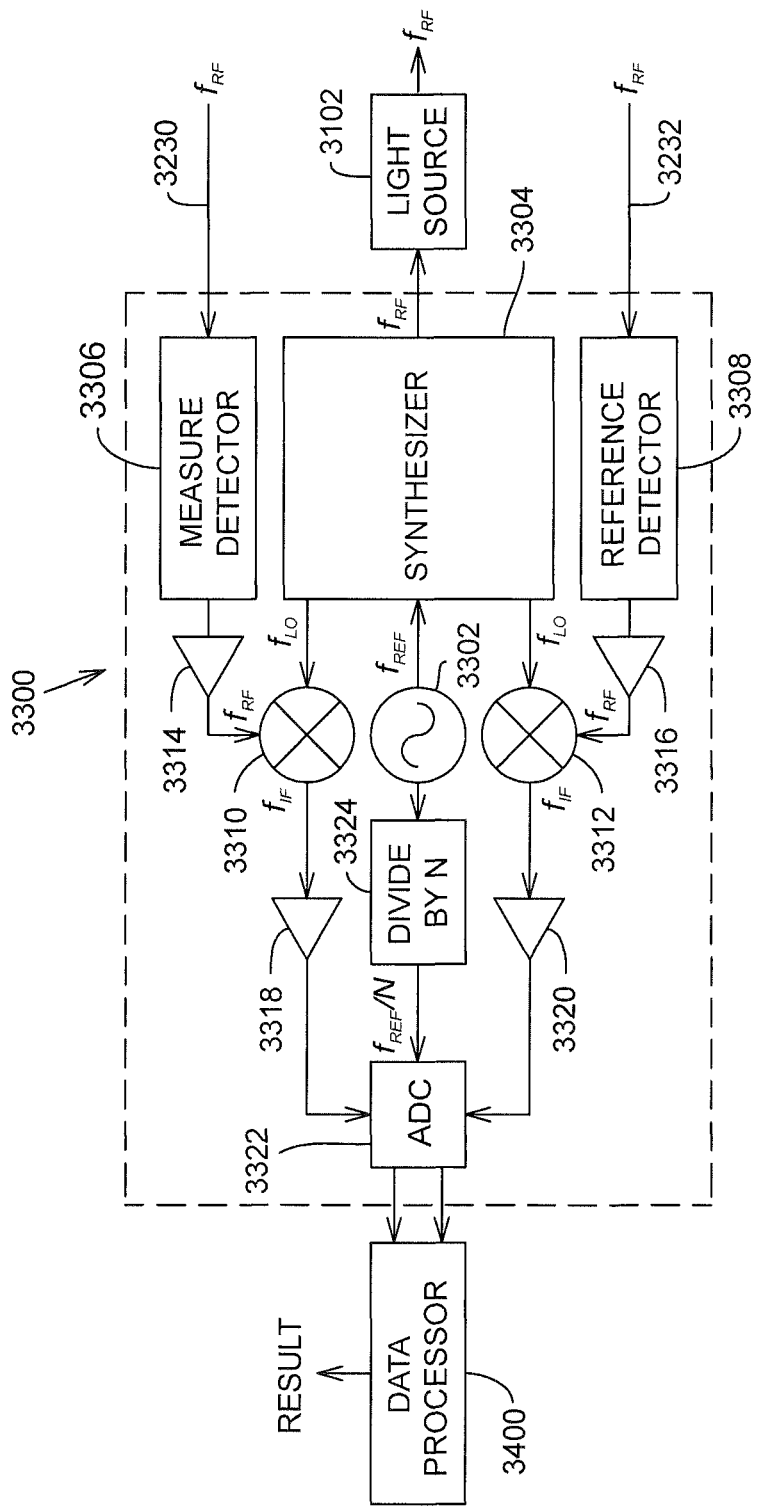
FIG. 7 is a block diagram of electrical and electro-optical elements within a prior art ADM.

The light from the fiber network 166 enters ADM electronics 164 through optical fibers 168, 169. An embodiment of prior art ADM electronics is shown in FIG. 7. Optical fiber 168 in FIG. 3 corresponds to optical fiber 3232 in FIG. 7, and optical fiber 169 in FIG. 3 corresponds to optical fiber 3230 in FIG. 7. Referring now to FIG. 7, ADM electronics 3300 includes a frequency reference 3302, a synthesizer 3304, a measure detector 3306, a reference detector 3308, a measure mixer 3310, a reference mixer 3312, conditioning electronics 3314, 3316, 3318, 3320, a divide-by-N prescaler 3324, and an analog-to-digital converter (ADC) 3322. The frequency reference, which might be an oven-controlled crystal oscillator (OCXO), for example, sends a reference frequency $f_{REF}$, which might be 10 MHz, for example, to the synthesizer, which generates two electrical signals—one signal at a frequency $f_{RF}$ and two signals at frequency $f_{LO}$. The signal $f_{RF}$ goes to the light source 3102, which corresponds to the light source 162 in FIG. 3. The two signals at frequency $f_{LO}$ go to the measure mixer 3310 and the reference mixer 3312. The light from optical fibers 168, 169 in FIG. 3 appear on fibers 3232, 3230 in FIG. 7, respectively, and enter the reference and measure channels, respectively. Reference detector 3308 and measure detector 3306 convert the optical signals into electrical signals. These signals are conditioned by electrical components 3316, 3314, respectively, and are sent to mixers 3312, 3310, respectively. The mixers produce a frequency $f_{IF}$ equal to the absolute value of $f_{LO}-f_{RF}$. The signal $f_{RF}$ may be a relatively high frequency, for example, 2 GHz, while the signal $f_{IF}$ may have a relatively low frequency, for example, 10 kHz.

The reference frequency $f_{REF}$ is sent to the prescaler 3324, which divides the frequency by an integer value. For example, a frequency of 10 MHz might be divided by 40 to obtain an output frequency of 250 kHz. In this example, the 10 kHz signals entering the ADC 3322 would be sampled at a rate of 250 kHz, thereby producing 25 samples per cycle. The signals from the ADC 3322 are sent to a data processor 3400, which might, for example, be one or more digital signal processor (DSP) units located in ADM electronics 164 of FIG. 3.

The method for extracting a distance is based on the calculation of phase of the ADC signals for the reference and measure channels. This method is described in detail in U.S. Pat. No. 7,701,559 ('559) to Bridges et al., the contents of which are herein incorporated by reference. Calculation includes use of equations (1)-(8) of patent '559. In addition, when the ADM first begins to measure a retroreflector, the frequencies generated by the synthesizer are changed some number of times (for example, three times), and the possible ADM distances calculated in each case. By comparing the possible ADM distances for each of the selected frequencies, an ambiguity in the ADM measurement is removed. The equations (1)-(8) of patent '559 combined with synchronization methods described with respect to FIG. 5 of patent '559 and the Kalman filter methods described in patent '559 enable the ADM to measure a moving target. In other embodiments, other methods of obtaining absolute distance measurements, for example, by using pulsed time-of-flight rather than phase differences, may be used.

The part of the return light beam 190 that passes through the beam splitter 155 arrives at the beam splitter 145, which sends part of the light to the beam expander 140 and another part of the light to the position detector assembly 150. The light emerging from the laser tracker 10 or EO system 100 may be thought of as a first beam and the portion of that light reflecting off the retroreflector 90 or 26 as a second beam. Portions of the reflected beam are sent to different functional elements of the EO system 100. For example, a first portion may be sent to a distance meter such as an ADM 160 in FIG. 3. A second portion may be sent to a position detector assembly 150. In some cases, a third portion may be sent to other functional units such as an optional interferometer (120). It is important to understand that, although, in the example of FIG. 3, the first portion and the second portion of the second beam are sent to the distance meter and the position detector after reflecting off beam splitters 155 and 145, respectively, it would have been possible to transmit, rather than reflect, the light onto a distance meter or position detector.

Figure 6F:
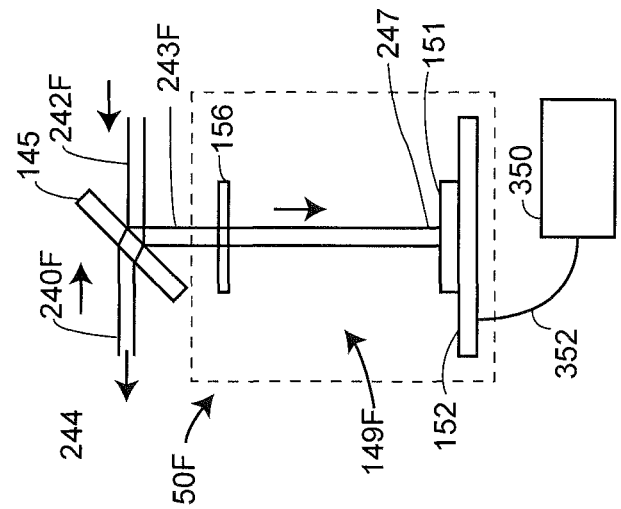
FIGS. 6E-F are schematic figures showing position detector assemblies according to embodiments of the present invention.

Four examples of prior art position detector assemblies 150A-150D are shown in FIGS. 6A-D. FIG. 6A depicts the simplest implementation, with the position detector assembly including a position sensor 151 mounted on a circuit board 152 that obtains power from and returns signals to electronics box 350, which may represent electronic processing capability at any location within the laser tracker 10, auxiliary unit 50, or external computer 60. FIG. 6B includes an optical filter 154 that blocks unwanted optical wavelengths from reaching the position sensor 151. The unwanted optical wavelengths may also be blocked, for example, by coating the beam splitter 145 or the surface of the position sensor 151 with an appropriate film. FIG. 6C includes a lens 153 that reduces the size of the beam of light. FIG. 6D includes both an optical filter 154 and a lens 153.

Figure 6E:
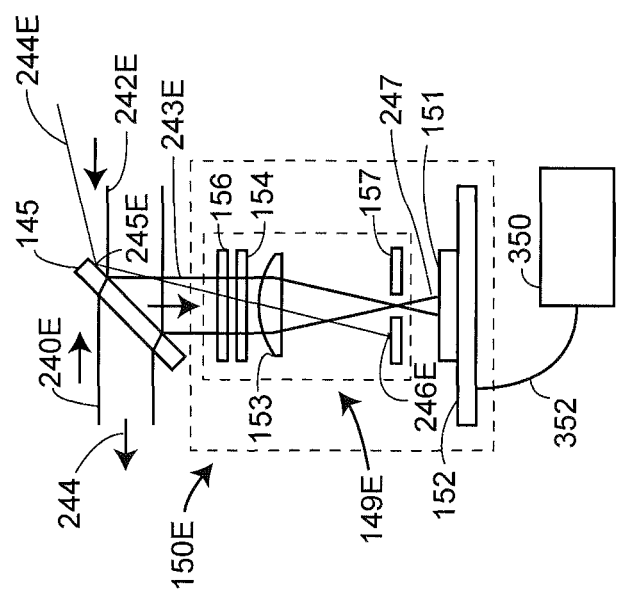

FIG. 6E shows a position detector assembly according to embodiments of the present invention that includes an optical conditioner 149E. Optical conditioner contains a lens 153 and may also contain optional wavelength filter 154. In addition, it includes at least one of a diffuser 156 and a spatial filter 157. As explained hereinabove, a popular type of retroreflector is the cube-corner retroreflector. One type of cube corner retroreflector is made of three mirrors, each joined at right angles to the other two mirrors. Lines of intersection at which these three mirrors are joined may have a finite thickness in which light is not perfectly reflected back to the tracker. The lines of finite thickness are diffracted as they propagate so that upon reaching the position detector they may not appear exactly the same as at the position detector. However, the diffracted light pattern will generally depart from perfect symmetry. As a result, the light that strikes the position detector 151 may have, for example, dips or rises in optical power (hot spots) in the vicinity of the diffracted lines. Because the uniformity of the light from the retroreflector may vary from retroreflector to retroreflector and also because the distribution of light on the position detector may vary as the retroreflector is rotated or tilted, it may be advantageous to include a diffuser 156 to improve the smoothness of the light that strikes the position detector 151. It might be argued that, because an ideal position detector should respond to a centroid and an ideal diffuser should spread a spot symmetrically, there should be no effect on the resulting position given by the position detector. However, in practice the diffuser is observed to improve performance of the position detector assembly, probably because the effects of nonlinearities (imperfections) in the position detector 151 and the lens 153. Cube corner retroreflectors made of glass may also produce non-uniform spots of light at the position detector 151. Variations in a spot of light at a position detector may be particularly prominent from light reflected from cube corners in six-DOF targets, as may be understood more clearly from commonly assigned U.S. patent application Ser. No. 13/370, 339 ('339) filed Feb. 10, 2012, and Ser. No. 13/407,983 ('983), filed Feb. 29, 2012, the contents of which are incorporated by reference herein. In an embodiment, the diffuser 156 is a holographic diffuser. A holographic diffuser provides controlled, homogeneous light over a specified diffusing angle. In other embodiments, other types of diffusers such as ground glass or "opal" diffusers are used.

The purpose of the spatial filter 157 of the position detector assembly 150E is to block ghost beams that may be the result, for example, of unwanted reflections off optical surfaces, from striking the position detector 151. A spatial filter includes a plate 157 that has an aperture. By placing the spatial filter 157 a distance away from the lens equal approximately to the focal length of the lens, the returning light 243E passes through the spatial filter when it is near its narrowest— at the waist of the beam. Beams that are traveling at a different angle, for example, as a result of reflection of an optical element strike the spatial filter away from the aperture and are blocked from reaching the position detector 151. An example is shown in FIG. 6E, where an unwanted ghost beam 244E reflects off a surface of the beam splitter 145 and travels to spatial filter 157, where it is blocked. Without the spatial filter, the ghost beam 244E would have intercepted the position detector 151, thereby causing the position of the beam 243E on the position detector 151 to be incorrectly determined. Even a weak ghost beam may significantly change the position of the centroid on the position detector 151 if the ghost beam is located a relatively large distance from the main spot of light.

A retroreflector of the sort discussed here, a cube corner or a cateye retroreflector, for example, has the property of reflecting a ray of light that enters the retroreflector in a direction parallel to the incident ray. In addition, the incident and reflected rays are symmetrically placed about the point of symmetry of the retroreflector. For example, in an open-air cube corner retroreflector, the point of symmetry of the retroreflector is the vertex of the cube corner. In a glass cube corner retroreflector, the point of symmetry is also the vertex, but one must consider the bending of the light at the glass-air interface in this case. In a cateye retroreflector having an index of refraction of 2.0, the point of symmetry is the center of the sphere. In a cateye retroreflector made of two glass hemispheres symmetrically seated on a common plane, the point of symmetry is a point lying on the plane and at the spherical center of each hemisphere. The main point is that, for the type of retroreflectors ordinarily used with laser trackers, the light returned by a retroreflector to the tracker is shifted to the other side of the vertex relative to the incident laser beam.

This behavior of a retroreflector 90 in FIG. 3 is the basis for the tracking of the retroreflector by the laser tracker. The position sensor has on its surface an ideal retrace point. The ideal retrace point is the point at which a laser beam sent to the point of symmetry of a retroreflector (e.g., the vertex of the cube corner retroreflector in an SMR) will return. Usually the retrace point is near the center of the position sensor. If the laser beam is sent to one side of the retroreflector, it reflects back on the other side and appears off the retrace point on the position sensor. By noting the position of the returning beam of light on the position sensor, the control system of the laser tracker 10 can cause the motors to move the light beam toward the point of symmetry of the retroreflector.

If the retroreflector is moved transverse to the tracker at a constant velocity, the light beam at the retroreflector will strike the retroreflector (after transients have settled) a fixed offset distance from the point of symmetry of the retroreflector. The laser tracker makes a correction to account for this offset distance at the retroreflector based on scale factor obtained from controlled measurements and based on the distance from the light beam on the position sensor to the ideal retrace point.

As explained hereinabove, the position detector performs two important functions—enabling tracking and correcting measurements to account for the movement of the retroreflector. The position sensor within the position detector may be any type of device capable of measuring a position. For example, the position sensor might be a position sensitive detector or a photosensitive array. The position sensitive detector might be lateral effect detector or a quadrant detector, for example. The photosensitive array might be a CMOS or CCD array, for example.

In an embodiment, the return light that does not reflect off beam splitter 145 passes through beam expander 140, thereby becoming smaller. In another embodiment, the positions of the position detector and the distance meter are reversed so that the light reflected by the beam splitter 145 travels to the distance meter and the light transmitted by the beam splitter travels to the position detector.

The light continues through optional IFM, through the isolator and into the visible light source 110. At this stage, the optical power should be small enough so that it does not destabilize the visible light source 110.

In an embodiment, the light from visible light source 110 is launched through a beam launch 170 of FIG. 5. The fiber launch may be attached to the output of light source 110 or a fiber optic output of the isolator 115.

In an embodiment, the fiber network 166 of FIG. 3 is prior art fiber network 420B of FIG. 8B. Here the optical fibers 184, 186, 168, 169 of FIG. 3 correspond to optical fibers 443, 444, 424, 422 of FIG. 8B. The fiber network of FIG. 8B is like the fiber network of FIG. 8A except that the fiber network of FIG. 8B has a single fiber coupler instead of two fiber couplers. The advantage of FIG. 8B over FIG. 8A is simplicity; however, FIG. 8B is more likely to have unwanted optical back reflections entering the optical fibers 422 and 424.

Figure 8C:
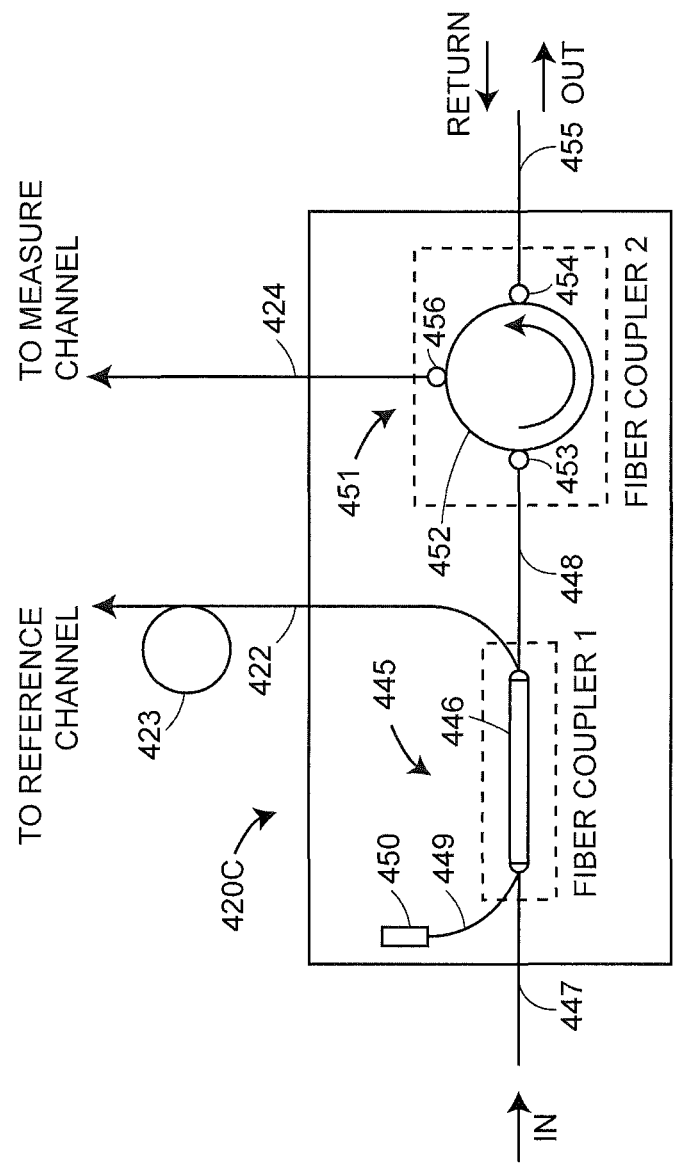
FIG. 8C is a schematic figure showing fiber-optic elements within a fiber-optic network in accordance with an embodiment of the present invention.

In an embodiment, the fiber network 166 of FIG. 3 is fiber network 420C of FIG. 8C. Here the optical fibers 184, 186, 168, 169 of FIG. 3 correspond to optical fibers 447, 455, 423, 424 of FIG. 8C. The fiber network 420C includes a first fiber coupler 445 and a second fiber coupler 451. The first fiber coupler 445 is a 2×2 coupler having two input ports and two output ports. Couplers of this type are usually made by placing two fiber cores in close proximity and then drawing the fibers while heated. In this way, evanescent coupling between the fibers can split off a desired fraction of the light to the adjacent fiber. The second fiber coupler 451 is of the type called a circulator. It has three ports, each having the capability of transmitting or receiving light, but only in the designated direction. For example, the light on optical fiber 448 enters port 453 and is transported toward port 454 as indicated by the arrow. At port 454, light may be transmitted to optical fiber 455. Similarly, light traveling on port 455 may enter port 454 and travel in the direction of the arrow to port 456, where some light may be transmitted to the optical fiber 424. If only three ports are needed, then the circulator 451 may suffer less losses of optical power than the 2×2 coupler. On the other hand, a circulator 451 may be more expensive than a 2×2 coupler, and it may experience polarization mode dispersion, which can be problematic in some situations.

Figure 9:
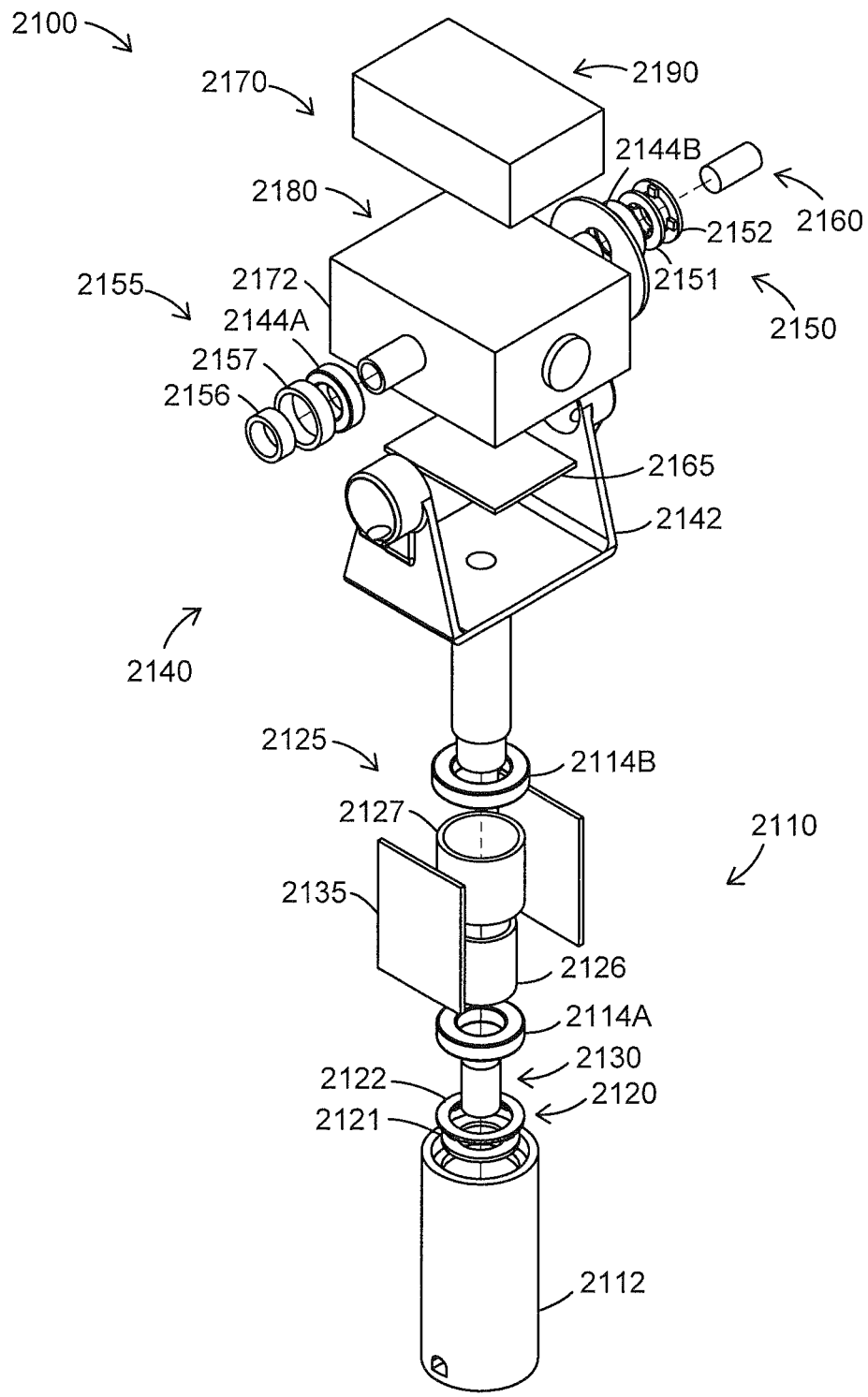
FIG. 9 is an exploded view of a prior art laser tracker.
Figure 10:
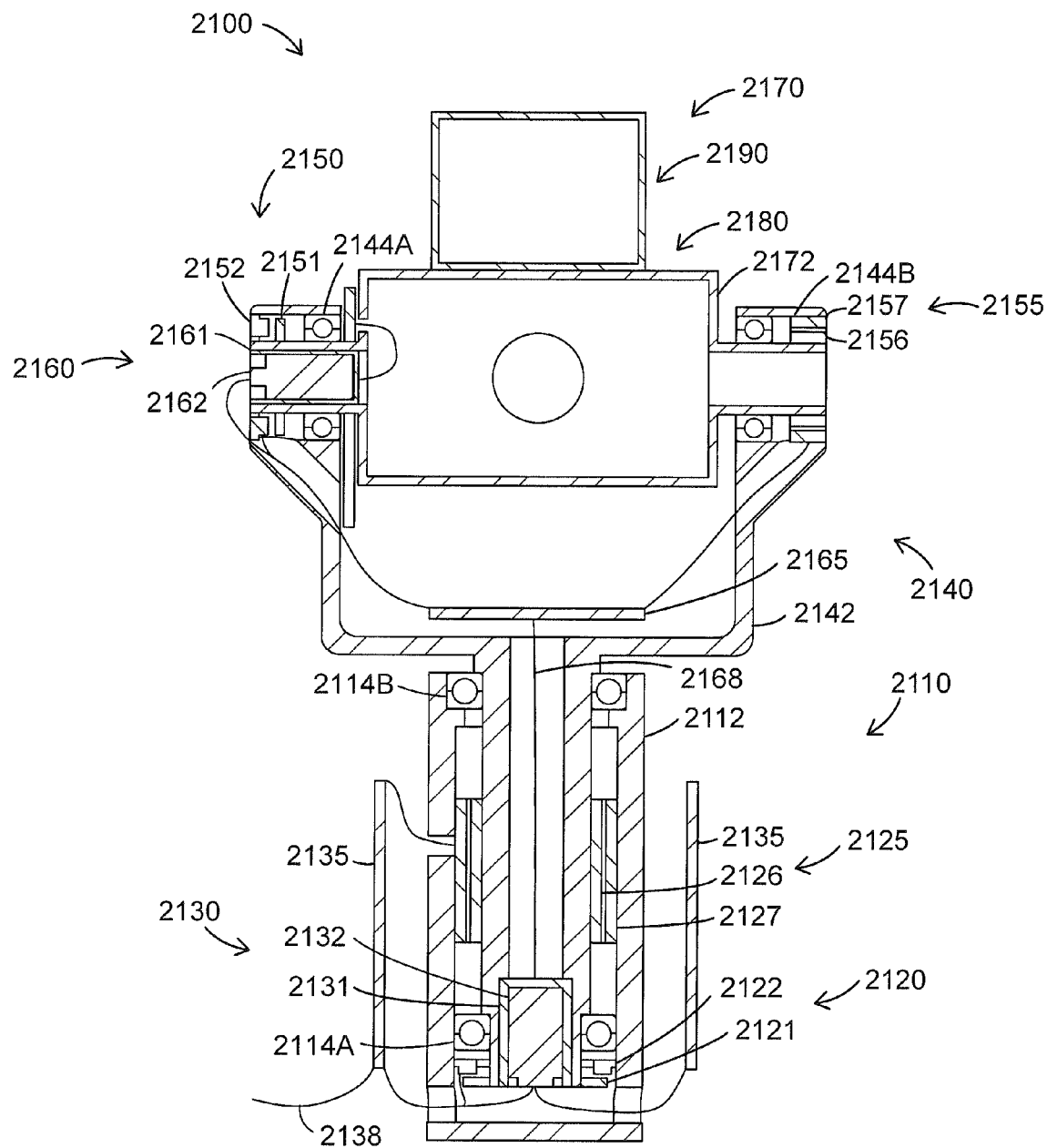
FIG. 10 is a cross-sectional view of a prior art laser tracker.

FIGS. 9 and 10 show exploded and cross sectional views, respectively, of a prior art laser tracker 2100, which is depicted in FIGS. 2 and 3 of U.S. Published Patent Application No. 2010/0128259 to Bridges et al., incorporated by reference herein. Azimuth assembly 2110 includes post housing 2112, azimuth encoder assembly 2120, lower and upper azimuth bearings 2114A, 2114B, azimuth motor assembly 2125, azimuth slip ring assembly 2130, and azimuth circuit boards 2135.

The purpose of azimuth encoder assembly 2120 is to accurately measure the angle of rotation of yoke 2142 with respect to the post housing 2112. Azimuth encoder assembly 2120 includes encoder disk 2121 and read-head assembly 2122. Encoder disk 2121 is attached to the shaft of yoke housing 2142, and read head assembly 2122 is attached to post assembly 2110. Read head assembly 2122 comprises a circuit board onto which one or more read heads are fastened. Laser light sent from read heads reflect off fine grating lines on encoder disk 2121. Reflected light picked up by detectors on encoder read head(s) is processed to find the angle of the rotating encoder disk in relation to the fixed read heads.

Azimuth motor assembly 2125 includes azimuth motor rotor 2126 and azimuth motor stator 2127. Azimuth motor rotor comprises permanent magnets attached directly to the shaft of yoke housing 2142. Azimuth motor stator 2127 comprises field windings that generate a prescribed magnetic field. This magnetic field interacts with the magnets of azimuth motor rotor 2126 to produce the desired rotary motion. Azimuth motor stator 2127 is attached to post frame 2112.

Azimuth circuit boards 2135 represent one or more circuit boards that provide electrical functions required by azimuth components such as the encoder and motor. Azimuth slip ring assembly 2130 includes outer part 2131 and inner part 2132. In an embodiment, wire bundle 2138 emerges from auxiliary unit processor 50. Wire bundle 2138 may carry power to the tracker or signals to and from the tracker. Some of the wires of wire bundle 2138 may be directed to connectors on circuit boards. In the example shown in FIG. 10, wires are routed to azimuth circuit board 2135, encoder read head assembly 2122, and azimuth motor assembly 2125. Other wires are routed to inner part 2132 of slip ring assembly 2130. Inner part 2132 is attached to post assembly 2110 and consequently remains stationary. Outer part 2131 is attached to yoke assembly 2140 and consequently rotates with respect to inner part 2132. Slip ring assembly 2130 is designed to permit low impedance electrical contact as outer part 2131 rotates with respect to the inner part 2132.

Zenith assembly 2140 comprises yoke housing 2142, zenith encoder assembly 2150, left and right zenith bearings 2144A, 2144B, zenith motor assembly 2155, zenith slip ring assembly 2160, and zenith circuit board 2165.

The purpose of zenith encoder assembly 2150 is to accurately measure the angle of rotation of payload frame 2172 with respect to yoke housing 2142. Zenith encoder assembly 2150 comprises zenith encoder disk 2151 and zenith read-head assembly 2152. Encoder disk 2151 is attached to payload housing 2142, and read head assembly 2152 is attached to yoke housing 2142. Zenith read head assembly 2152 comprises a circuit board onto which one or more read heads are fastened. Laser light sent from read heads reflect off fine grating lines on encoder disk 2151. Reflected light picked up by detectors on encoder read head(s) is processed to find the angle of the rotating encoder disk in relation to the fixed read heads.

Zenith motor assembly 2155 comprises zenith motor rotor 2156 and zenith motor stator 2157. Zenith motor rotor 2156 comprises permanent magnets attached directly to the shaft of payload frame 2172. Zenith motor stator 2157 comprises field windings that generate a prescribed magnetic field. This magnetic field interacts with the rotor magnets to produce the desired rotary motion. Zenith motor stator 2157 is attached to yoke frame 2142.

Zenith circuit board 2165 represents one or more circuit boards that provide electrical functions required by zenith components such as the encoder and motor. Zenith slip ring assembly 2160 comprises outer part 2161 and inner part 2162. Wire bundle 2168 emerges from azimuth outer slip ring 2131 and may carry power or signals. Some of the wires of wire bundle 2168 may be directed to connectors on circuit board. In the example shown in FIG. 10, wires are routed to zenith circuit board 2165, zenith motor assembly 2150, and encoder read head assembly 2152. Other wires are routed to inner part 2162 of slip ring assembly 2160. Inner part 2162 is attached to yoke frame 2142 and consequently rotates in azimuth angle only, but not in zenith angle. Outer part 2161 is attached to payload frame 2172 and consequently rotates in both zenith and azimuth angles. Slip ring assembly 2160 is designed to permit low impedance electrical contact as outer part 2161 rotates with respect to the inner part 2162. Payload assembly 2170 includes a main optics assembly 2180 and a secondary optics assembly 2190.

Figure 11:
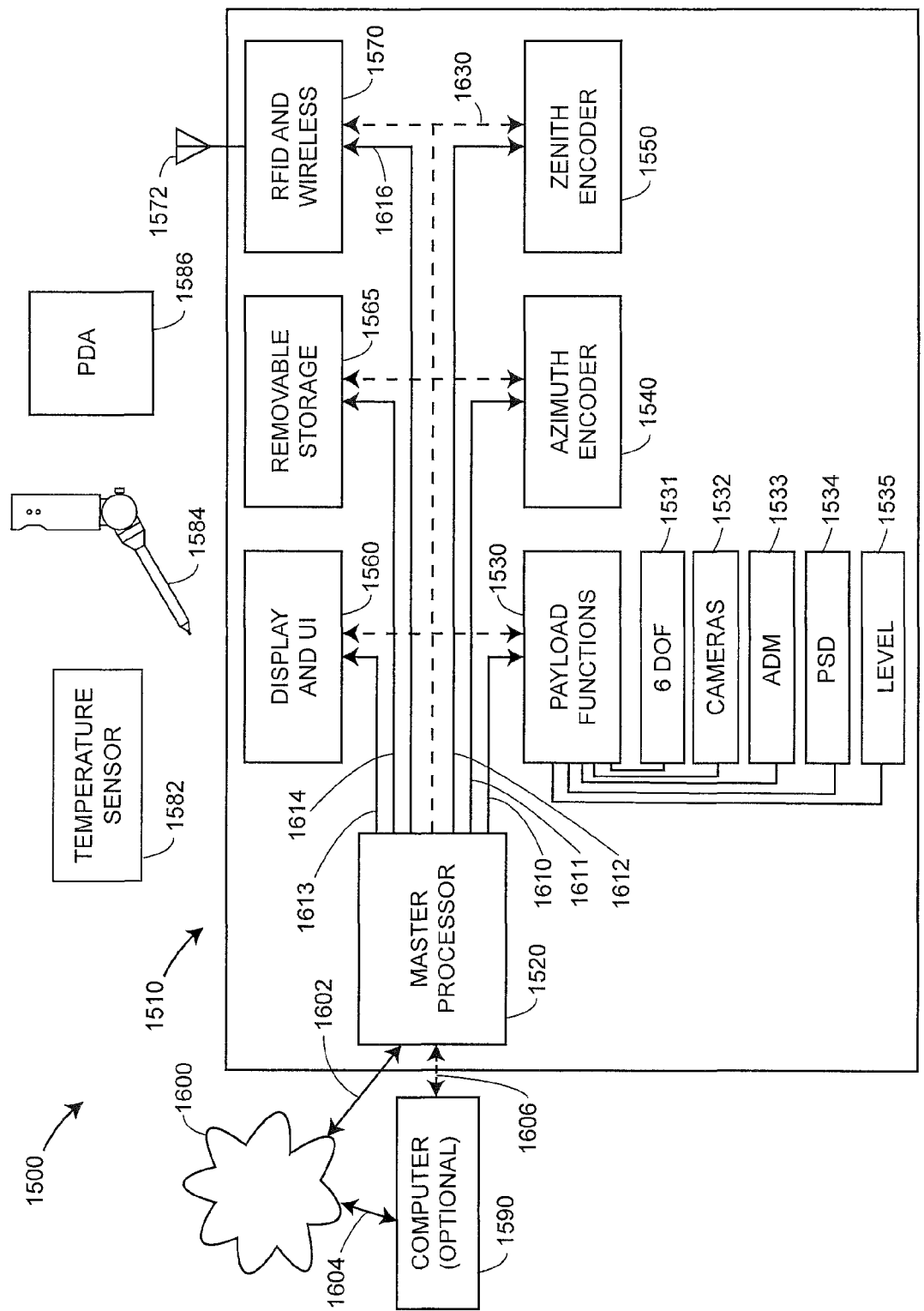
FIG. 11 is a block diagram of the computing and communication elements of a laser tracker in accordance with an embodiment of the present invention.

FIG. 11 is a block diagram depicting a dimensional measurement electronics processing system 1500 that includes a laser tracker electronics processing system 1510, processing systems of peripheral elements 1582, 1584, 1586, computer 1590, and other networked components 1600, represented here as a cloud. Exemplary laser tracker electronics processing system 1510 includes a master processor 1520, payload functions electronics 1530, azimuth encoder electronics 1540, zenith encoder electronics 1550, display and user interface (UI) electronics 1560, removable storage hardware 1565, radio frequency identification (RFID) electronics, and an antenna 1572. The payload functions electronics 1530 includes a number of subfunctions including the six-DOF electronics 1531, the camera electronics 1532, the ADM electronics 1533, the position detector (PSD) electronics 1534, and the level electronics 1535. Most of the subfunctions have at least one processor unit, which might be a digital signal processor (DSP) or field programmable gate array (FPGA), for example. The electronics units 1530, 1540, and 1550 are separated as shown because of their location within the laser tracker. In an embodiment, the payload functions 1530 are located in the payload 2170 of FIGS. 9 and 10, while the azimuth encoder electronics 1540 is located in the azimuth assembly 2110 and the zenith encoder electronics 1550 is located in the zenith assembly 2140.

Many types of peripheral devices are possible, but here three such devices are shown: a temperature sensor 1582, a six-DOF probe 1584, and a personal digital assistant, 1586, which might be a smart phone, for example. The laser tracker may communicate with peripheral devices in a variety of means, including wireless communication over the antenna 1572, by means of a vision system such as a camera, and by means of distance and angular readings of the laser tracker to a cooperative target such as the six-DOF probe 1584. Peripheral devices may contain processors. The six-DOF accessories may include six-DOF probing systems, six-DOF scanners, six-DOF projectors, six-DOF sensors, and six-DOF indicators. The processors in these six-DOF devices may be used in conjunction with processing devices in the laser tracker as well as an external computer and cloud processing resources. Generally, when the term laser tracker processor or measurement device processor is used, it is meant to include possible external computer and cloud support.

In an embodiment, a separate communications bus goes from the master processor 1520 to each of the electronics units 1530, 1540, 1550, 1560, 1565, and 1570. Each communications line may have, for example, three serial lines that include the data line, clock line, and frame line. The frame line indicates whether or not the electronics unit should pay attention to the clock line. If it indicates that attention should be given, the electronics unit reads the current value of the data line at each clock signal. The clock-signal may correspond, for example, to a rising edge of a clock pulse. In an embodiment, information is transmitted over the data line in the form of a packet. In an embodiment, each packet includes an address, a numeric value, a data message, and a checksum. The address indicates where, within the electronics unit, the data message is to be directed. The location may, for example, correspond to a processor subroutine within the electronics unit. The numeric value indicates the length of the data message. The data message contains data or instructions for the electronics unit to carry out. The checksum is a numeric value that is used to minimize the chance that errors are transmitted over the communications line.

In an embodiment, the master processor 1520 sends packets of information over bus 1610 to payload functions electronics 1530, over bus 1611 to azimuth encoder electronics 1540, over bus 1612 to zenith encoder electronics 1550, over bus 1613 to display and UI electronics 1560, over bus 1614 to removable storage hardware 1565, and over bus 1616 to RFID and wireless electronics 1570.

In an embodiment, master processor 1520 also sends a synch (synchronization) pulse over the synch bus 1630 to each of the electronics units at the same time. The synch pulse provides a way of synchronizing values collected by the measurement functions of the laser tracker. For example, the azimuth encoder electronics 1540 and the zenith electronics 1550 latch their encoder values as soon as the synch pulse is received. Similarly, the payload functions electronics 1530 latch the data collected by the electronics contained within the payload. The six-DOF, ADM, and position detector all latch data when the synch pulse is given. In most cases, the camera and inclinometer collect data at a slower rate than the synch pulse rate but may latch data at multiples of the synch pulse period.

The azimuth encoder electronics 1540 and zenith encoder electronics 1550 are separated from one another and from the payload electronics 1530 by the slip rings 2130, 2160 shown in FIGS. 9 and 10. For this reason the bus lines 1610, 1611, and 1612 are illustrated as separate bus lines in FIG. 11.

The laser tracker electronics processing system 1510 may communicate with an external computer 1590, or it may provide computation, display, and UI functions within the laser tracker. The laser tracker communicates with computer 1590 over communications link 1606, which might be, for example, an Ethernet line or a wireless connection. The laser tracker may also communicate with other elements 1600, represented by the cloud, over communications link 1602, which might include one or more electrical cables, such as Ethernet cables, and one or more wireless connections. An example of an element 1600 is another three dimensional test instrument—for example, an articulated arm CMM, which may be relocated by the laser tracker. A communication link 1604 between the computer 1590 and the elements 1600 may be wired (e.g., Ethernet) or wireless. An operator sitting on a remote computer 1590 may make a connection to the Internet, represented by the cloud 1600, over an Ethernet or wireless line, which in turn connects to the master processor 1520 over an Ethernet or wireless line. In this way, a user may control the action of a remote laser tracker.

Figure 12:
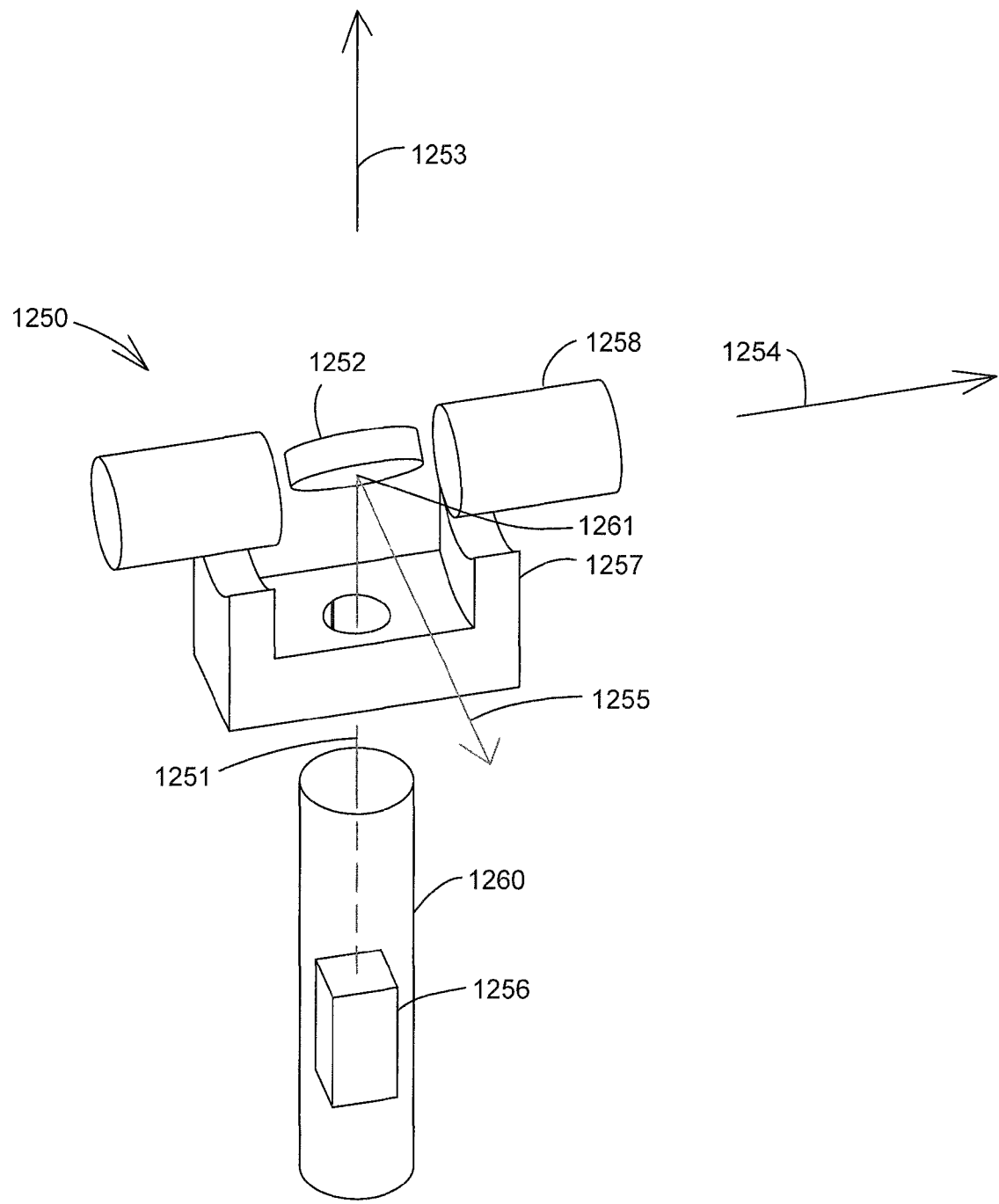
FIG. 12 is a perspective view of some internal elements within a laser tracker that steers a beam of light using a mirror according to an embodiment of the present invention.

FIG. 12 shows an embodiment of a laser tracker 1250 that uses a mirror 1252 to steer a beam of light 1251, 1255 from the tracker. The assembly 1256 may include a variety of optical, electrical, and mechanical components design to produce one or more beams of light, control the direction of the beam of light to enable tracking of a retroreflector target, and measure the distance to the target. In addition, functions provided within the laser tracker 1250 include using motors to turn the axles 1260, 1258 about first axis 1253 and second axis 1254, respectively, and using angular encoders to measure the angles of rotation about the first axis and second axis. The laser tracker 1250 of FIG. 12 is similar to the laser tracker described in FIGS. 9 and 10 in having a gimbal point 1261, which in the point at which the mechanical axes 1253 and 1254 substantially intersect. In addition, in both types of trackers, the laser beam passes, at least virtually through the gimbal point.

It is possible to use other mechanical arrangements that have a gimbal point but are configured somewhat differently. For example, it is possible to emit a beam of light in the horizontal direction along an axis equivalent to 1254 and to angle the mirror at 45 degrees with respect to the beam of light so that the mirror reflects the light in the same direction as the beam in 1255. For the present application, the rotation about each of two axes is made possible by the rotation of an axle aligned to each axis, wherein each of the two axles is mounted on a pair of spaced bearings.

In the discussion above, it was stated that the mechanical axes substantially intersect at a point called a gimbal point. The two mechanical axes do not exactly intersect in a point; rather there is a slight separation between the two mechanical axes, which at the point of closest approach of the two axes is called the axis offset. To correct for the slight error caused by axis offset, a compensation parameter may be stored for axis offset. Software in a tracker processor or an external computer may then correct the data collected by the tracker to remove the error caused by the axis offset. In effect, the tracker creates a model of a perfect tracker in which the two axes intersect at an ideal gimbal point.

In the discussion above, it was stated that the beam of light from the tracker passes, at least virtually through the gimbal point. In practice, the beam of light may be slightly offset with respect to the gimbal point. In an embodiment, this offset is accounted for by using two compensation parameters, TX and TY. In an ideal tracker, the laser beam lies in a plane that contains the vertical (azimuth) axis and is perpendicular to the horizontal (zenith) axis. In a real tracker, the laser beam may be angled slightly with respect to this plane. This offset may be accounted for with two compensation parameters RX and RY. Many other compensation parameters are possible, and different names may be used to describe these parameters. For example, there may be an axis non-squareness (AXNS) parameter that denotes the deviation of the nominally perpendicular axes from ninety degrees. There may be parameters associated with a mirror, for example a position of the mirror surface relative to the horizontal axis. Parameters associated with laser trackers may include those described in the paper by Muralikrishnan, et al., "ASME B89.4.19 Performance Evaluation Tests and Geometric Misalignments in Laser Trackers," J. Res. Natl. Inst. Stand. Technol. 114, 21-35 (2009), which is incorporated herein by reference in its entirety.

Figure 13:
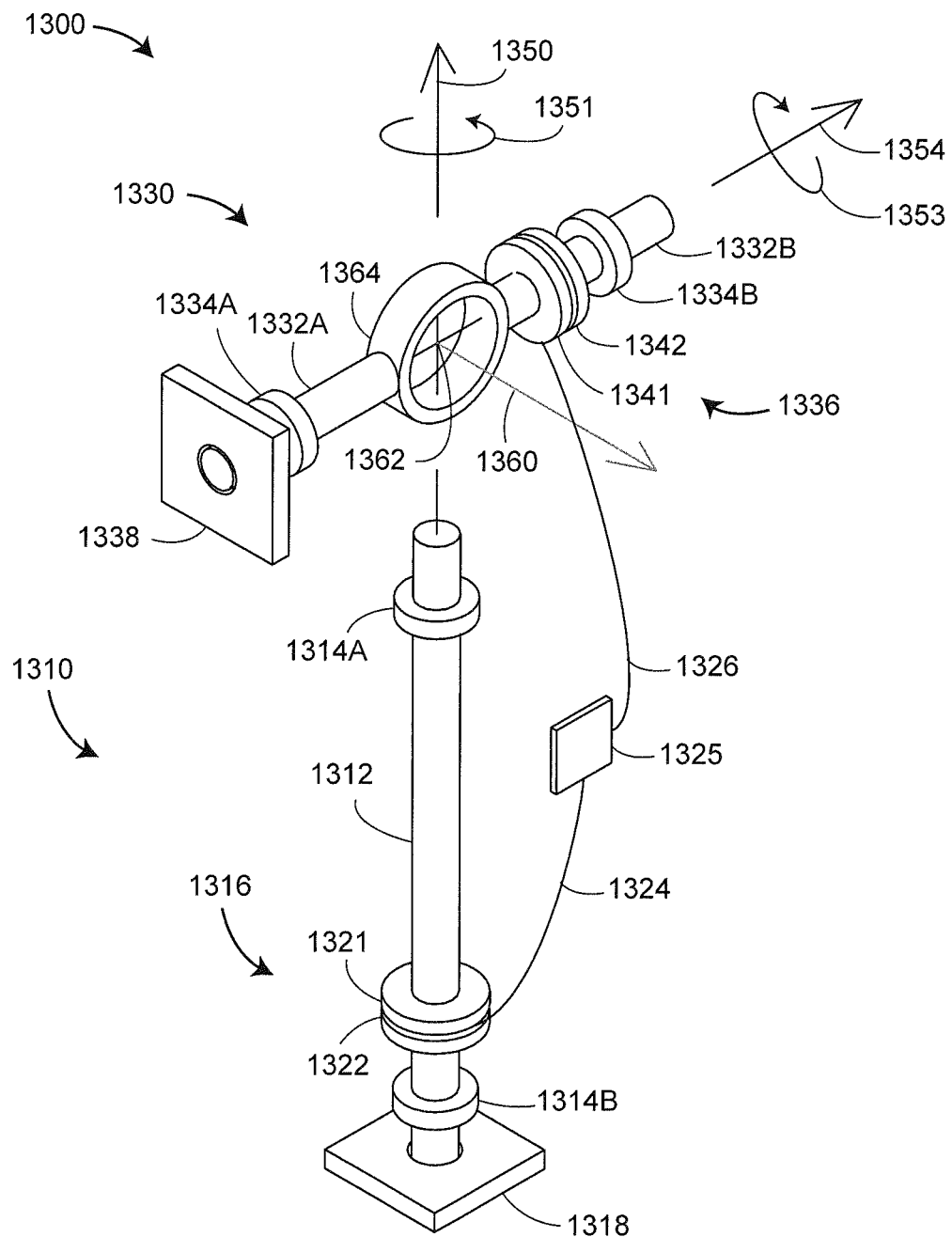
FIG. 13 is a perspective view of some elements within a laser tracker according to an embodiment of the present invention.

FIG. 13 is a perspective view of selected elements 1300 within a laser tracker according to an embodiment. Azimuth/base assembly 1310 includes an azimuth axle 1312, a first bearing 1314A, a second bearing 1314B, an angular encoder 1316, and base frame 1318. The base frame 1318 represents that portion of the laser tracker that is fixed with respect to the surroundings within which the tracker resides. For example, in operation, the laser tracker may be mounted on an instrument stand, with the base frame 1318 fixed with respect to the instrument stand. The axle 1312 rotates in a circular motion 1351 about an azimuth axis 1350. The angular encoder 1316 includes a disk 1321 and a read-head assembly 1322. The disk 1321 includes markings, which in an embodiment includes evenly spaced lines directed away from the disk center. The read-head assembly 1322 includes one or more sources of light. The sources of light are either reflected off the surface of the disk 1321 or transmitted through the disk. The read-head assembly also includes one or more optical detectors that sense when light has passed a marking on the disk. In an embodiment, the disk is mounted on the axle 1312 and the read-head assembly is mounted on a fixed portion of the azimuth/base assembly. In other words, the read-head assembly is attached is stationary with respect to the base frame 1318. In an alternative embodiment, the disk is fixed and the read-head assembly is attached to the axle. By counting the lines that have passed the one or more optical detectors on the read-head assembly 1322 and by using interpolation electronics, the encoder and associated electronics can determine the angle of rotation of the axle 1312 to relatively high accuracy. Electrical signals travel from the read-head assembly 1322 over electrical line 1324 to an electronics board 1325 that processes the signal to determine the angle of rotation of the axle 1312. The electronics board 1325 may contain a processor 1540 as shown in FIG. 11.

In an embodiment, the azimuth bearings 1314A, 1314B are angular contact ball bearings. The bearings may have an inner race and an outer race that come as separate elements. In an embodiment, each bearing is marked with a runout high point. The bearings 1314A, 1314 B are rotated so that the runout high points are in the same angular position on the azimuth axle 1312. In an embodiment, the azimuth/base assembly is configured to enable application of a controlled preload force to the bearings 1314A, 1314B.

Zenith/yoke assembly 1330 includes a zenith axle 1332A, 1332B, a first bearing 1334A, a second bearing 1334B, an angular encoder 1336, and a yoke frame 1338. The yoke frame 1338 represents that portion of the laser tracker that rotates along with the azimuth axle 1312. The yoke frame is a portion of the zenith carriage assembly, discussed hereinabove. The axle 1332A, 1332B rotates in a circular motion 1353 about an azimuth axis 1354. The angular encoder 1336 includes a disk 1341 and a read-head assembly 1342. The disk 1341 includes markings, which in an embodiment includes evenly spaced lines directed away from the disk center. The read-head assembly 1342 includes one or more sources of light. The sources of light are either reflected off the surface of the disk 1341 or transmitted through the disk. The read-head assembly also includes one or more optical detectors that sense when light has passed a marking on the disk. In an embodiment, the disk is mounted on the zenith axle 1342 and the read-head assembly is mounted on a portion of the zenith assembly that rotates with the azimuth axle 1312. In other words, the read-head assembly 1342 is stationary with respect to the yoke frame 1338. In an alternative embodiment, the disk is fixed and the read-head assembly is attached to the zenith axle. By counting the lines that have passed the one or more optical detectors on the read-head assembly 1342 and by using interpolation electronics, the encoder and associated electronics can determine the angle of rotation of the axle 1332 to relatively high accuracy. Electrical signals travel from the read-head assembly 1342 over electrical line 1326 to the electronics board 1325 that processes the signal to determine the angle of rotation of the axle 1332. The electronics board 1325 may include a processor 1550 as shown in FIG. 11. The zenith/yoke assembly 1330 may contain one or more light sources (not shown) that produce a beam of light 1360. As explained hereinabove, the light beam 1360 may virtually (or actually) pass through a gimbal point 1362. The axle may contain two parts (1332A, 1332B) that are collinear but are supported in the center by a payload structure 1364, a portion of which is shown in FIG. 13. The payload structure may support the light source, optical elements such as lenses and beam splitters, a position detector, a control system, distance meters, electronics, and accessory components such as inclinometers and temperature sensors. Alternatively, laser light may be routed to the payload region by optical fibers located outside the payload or by other means.

In an embodiment, the zenith bearings 1334A, 1334B are angular contact ball bearings. The bearings may have an inner race and an outer race that come as separate elements. In an embodiment, the bearings 1334A, 1334 B are rotated so that the runout high points are in the same angular position on the azimuth axle 1312 to minimize the angular wobble caused by bearing runout. In an embodiment, the azimuth/base assembly is configured to enable application of a controlled preload force to the bearings 1334A, 1334B.

Figure 14:
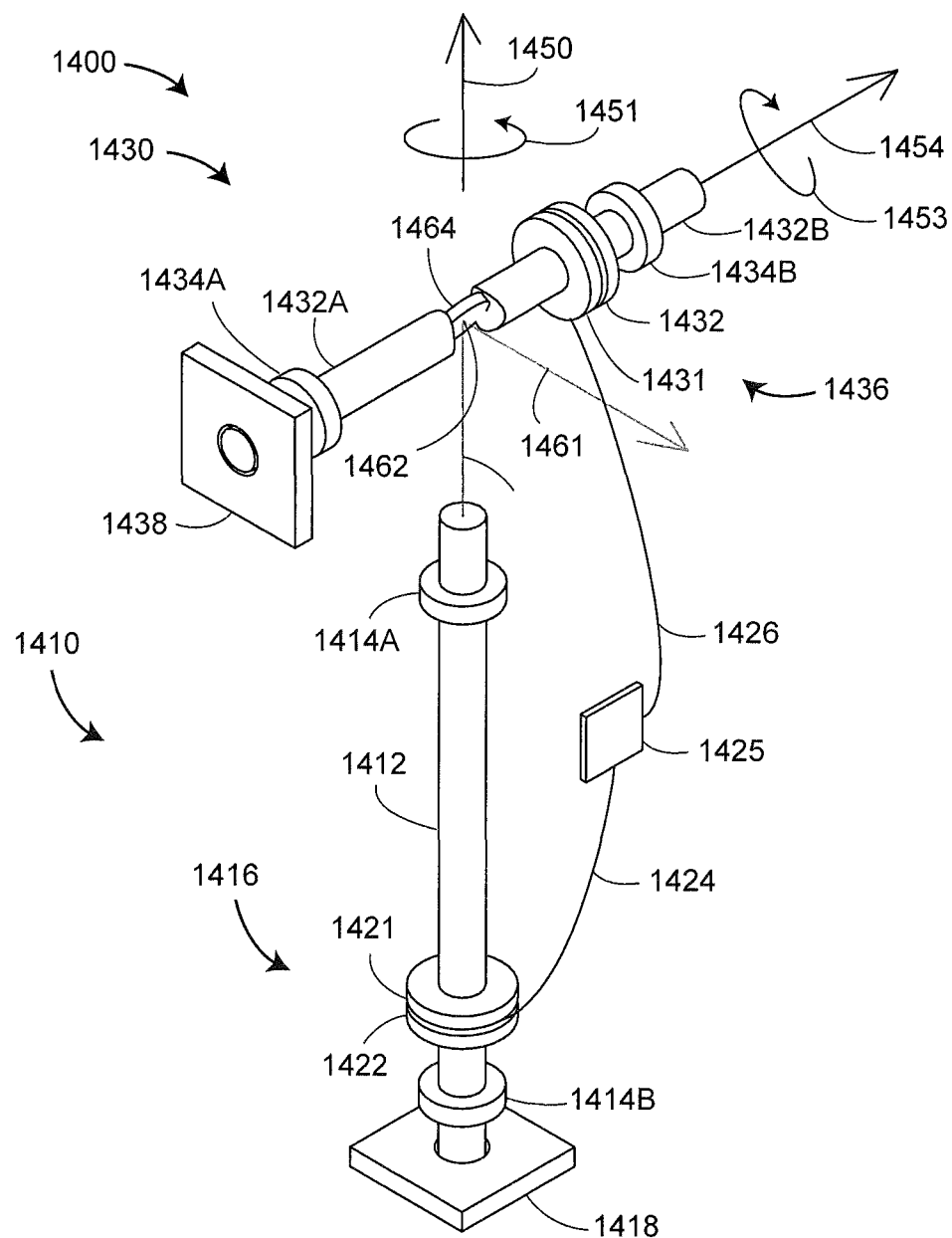
FIG. 14 is a perspective view of some elements within a laser tracker according to an embodiment of the present invention.

FIG. 14 is a perspective view of selected elements 1400 within a laser tracker according to an embodiment. The laser tracker of FIG. 14 is similar to the laser tracker of FIG. 13 except that the laser tracker of FIG. 14 directs a beam of light partly by reflecting the beam of light off a mirror 1462 while the laser tracker of FIG. 13 directs the beam directly out of a payload structure 1364. Azimuth/base assembly 1410 includes an azimuth axle 1412, a first bearing 1414A, a second bearing 1414B, an angular encoder 1416, and base frame 1418. The base frame 1418 represents that portion of the laser tracker that is fixed with respect to the surroundings within which the tracker resides. For example, in operation, the laser tracker may be mounted on an instrument stand, with the base frame 1418 fixed with respect to the instrument stand. The axle 1412 rotates in a circular motion 1451 about an azimuth axis 1450. The angular encoder 1416 includes a disk 1421 and a read-head assembly 1422. The disk 1421 includes markings, which in an embodiment includes evenly spaced lines directed away from the disk center. The read-head assembly 1422 includes one or more sources of light. The sources of light are either reflected off the surface of the disk 1421 or transmitted through the disk. The read-head assembly also includes one or more optical detectors that sense when light has passed a marking on the disk. In an embodiment, the disk is mounted on the axle 1412 and the read-head assembly is mounted on a fixed portion of the azimuth/base assembly. In other words, the read-head assembly is stationary with respect to the base frame 1418. In an alternative embodiment, the disk is fixed and the read-head assembly is attached to the axle. By counting the lines that have passed the one or more optical detectors on the read-head assembly 1422 and by using interpolation electronics, the encoder and associated electronics can determine the angle of rotation of the axle 1412 to relatively high accuracy. Electrical signals travel from the read-head assembly 1422 over electrical line 1424 to an electronics board 1425 that processes the signal to determine the angle of rotation of the axle 1412. The electronics board 1425 may contain a processor 1540 as shown in FIG. 11.

In an embodiment, the azimuth bearings 1414A, 1414B are angular contact ball bearings. The bearings may have an inner race and an outer race that come as separate elements. In an embodiment, the bearings 1414A, 1414 B are rotated so that the runout high points are in the same angular position on the azimuth axle 1412 to minimize angular wobble caused by bearing runout. In an embodiment, the azimuth/base assembly is configured to enable application of a controlled preload force to the bearings 1414A, 1414B.

Zenith/yoke assembly 1430 includes a zenith axle 1432A, 1432B, a first bearing 1434A, a second bearing 1434B, an angular encoder 1436, and a yoke frame 1438. The yoke frame 1438 represents that portion of the laser tracker that rotates along with the azimuth axle 1412. The yoke frame is a portion of the zenith carriage assembly, discussed hereinabove. The axle 1432A, 1432B rotates in a circular motion 1453 about an azimuth axis 1454. The angular encoder 1436 includes a disk 1441 and a read-head assembly 1442. The disk 1441 includes markings, which in an embodiment includes evenly spaced lines directed away from the disk center. The read-head assembly 1442 includes one or more sources of light. The sources of light are either reflected off the surface of the disk 1441 or transmitted through the disk. The read-head assembly also includes one or more optical detectors that sense when light has passed a marking on the disk. In an embodiment, the disk is mounted on the zenith axle 1442 and the read-head assembly is mounted on a portion of the zenith assembly that rotates with the azimuth axle 1412. In other words, the read-head assembly 1442 is attached is stationary with respect to the yoke frame 1438. In an alternative embodiment, the disk is fixed and the read-head assembly is attached to the zenith axle. By counting the lines that have passed the one or more optical detectors on the read-head assembly 1442 and by using interpolation electronics, the encoder and associated electronics can determine the angle of rotation of the axle 1432 to relatively high accuracy. Electrical signals travel from the read-head assembly 1442 over electrical line 1426 to the electronics board 1425 that processes the signal to determine the angle of rotation of the axle 1432. The electronics board 1425 may include a processor 1550 as shown in FIG. 11. The azimuth/base assembly 1410 may contain one or more light sources (not shown) that produce a beam of light 1460 that is reflected by mirror 1464. As explained hereinabove, the light beam 1461 may reflect at a gimbal point 1462. The axle may contain two parts (1432A, 1432B) that are collinear and support the mirror 1464. Light sources, optics, and electronics may reside within a hollow axle 1412 or be reflected off beam splitters and mirrors to produce beam 1460 and process the returning light. Optics and electronics may also include lenses, a position detector, a control system, distance meters, electronics, and accessory components such as inclinometers and temperature sensors.

In an embodiment, the zenith bearings 1434A, 1434B are angular contact ball bearings. The bearings may have an inner race and an outer race that come as separate elements. In an embodiment, each bearing is marked with a runout high point. The bearings 1434A, 1434 B are rotated so that the runout high points are in the same angular position on the azimuth axle 1412. In an embodiment, the azimuth/base assembly is configured to enable application of a controlled preload force to the bearings 1434A, 1434B.

FIGS. 15A and 15B are perspective views of a prior art apparatus 3500 that may be attached to a laser tracker to measure bearing errors of a laser tracker to which it is attached. The apparatus includes a rotating assembly 3510 and a fixed assembly 3540. The rotating assembly 3510 includes a first shaft portion 3512, a second shaft portion 3513, a first sphere portion 3514, and a second sphere portion 3516. The first shaft portion has a surface 3511 that attaches to a rotating structure. In an embodiment, the surface 3511 attaches to transfer element (not shown) which is then attached to a rotating structure under test. In an embodiment, the spheres are lapped to a form error of 50 nanometers or less. The first sphere portion 3514 has a first equator 3515 that is a great circle of the sphere and is aligned perpendicular to the first and second shaft portions. The second sphere portion 3516 has a first equator 3517 that is a great circle of the sphere and is aligned perpendicular to the first and second shaft portions. The fixed assembly 3540 includes a frame 3542 and a plurality of capacitive sensors 3544, 3545, 3546, 3547, 3548 rigidly affixed to the frame 3542. Electrical connections 3534, 3535, 3536, 3537, 3538 travel from the sensors 3544, 3545, 3546, 3547, 3548, respectively, to an electrical circuit (not shown) for processing. In an embodiment, capacitive sensors 3544, 3545 are aligned perpendicular to the first sphere portion at the level of the first equator. The capacitive sensors 3544, 3545 are moved slightly away from the sphere to prevent collision with the sensors during rotation. The capacitive sensor 3514 is rotated ninety degrees from capacitive sensor 3515. The fixed assembly 3540 is attached to a non-rotating structure. In an embodiment, the frame 3542 is attached to the fixed structure that holds the rotating object (the spindle or axle).

In an embodiment, capacitive sensors 3546, 3547 are aligned perpendicular to the second sphere portion 3516 at the level of the first equator 3517. The capacitive sensors 3546, 3547 are moved slightly away from the sphere to prevent collision with the sensors during rotation. The capacitive sensor 3546 is rotated ninety degrees from capacitive sensor 3547. In an embodiment, the capacitive sensor 3548 is aligned along the axis of the second sphere portion 3516 and the second shaft portion 3512. In an alternative embodiment, the capacitive sensor 3548 is not included in the apparatus 3500. In other embodiments, the capacitive sensors are aligned to one or more cylindrical artifacts rather than spherical artifacts 3514, 3516.

FIG. 15B depicts an axis of rotation z and an angle of rotation θ. The angle θ is taken with respect to an axis x perpendicular to the z axis. The first sphere portion 3514 has first frame of reference 3570 that includes an origin 3571 at the center of the spherical surface of the first sphere portion. The first frame of reference 3570 has an axis $z_1$ aligned with the axis of the first and second shaft portions and with the axis z. The axis $x_1$ is aligned with the capacitive sensor 3544, and the axis $y_1$ is aligned with the capacitive sensor 3545. The axes $x_1$, $y_1$, and $z_1$ are mutually perpendicular.

The second sphere portion 3516 has second frame of reference 3580 that includes an origin 3581 at the center of the spherical surface of the second sphere portion. The second frame of reference 3580 has an axis $z_1$ aligned with the axis of the first and second shaft portions and with the axis z. The axis $x_2$ is aligned with the capacitive sensor 3546, and the axis $y_2$ is aligned with the capacitive sensor 3547. The axes $x_2$, $y_2$, and $z_2$ are mutually perpendicular. The capacitive sensor 3548 is aligned with the z axis near the bottom of the second sphere portion 3516. The distance between the first origin 3571 and the second origin 3581 along the z direction is L.

For each angle θ, the apparatus 3500 measures five displacements are measured for each of the five capacitive sensors 3544, 3545, 3546, 3547, 3548. These displacements are $\Delta x_1$, $\Delta y_1$, $\Delta x_2$, $\Delta y_2$, and $\Delta z_2$, respectively. From these displacements, tilt angles $\alpha_x$ and $\alpha_y$ resulting from the bearing errors may be obtained:

$$\alpha_x = (\Delta x_1 - \Delta x_2)/L, \quad (1)$$

$$\alpha_y = (\Delta y_1 - \Delta y_2)/L. \quad (2)$$

In the past, bearing calibration techniques have been used mostly for measuring high speed spindles of precision machining tools, especially diamond turning machines, but also a variety of lathes, milling machines, grinders, and the like. Usually bearing calibrations are performed first to ensure that a machine tool meets its specifications and second to find ways to change machine tool design to improve tool performance. Because machine tools cannot be adjusted while machining operations are performed, it is not usually possible to correct the behavior of the machine tools while machining operations are underway.

For any 360 degree rotation of a quality bearing, it is usually the case that bearing error repeats almost exactly as a function of the rotation angle θ. In other words, if the bearing is moved back and forth over the same 360 degree window, the pattern of errors recorded by the capacitive sensors is almost the same for any given angle θ. However, for the most part bearing errors do not repeat over different cycles of 360 degrees. This behavior is explained in a tutorial on "Precision Spindle Metrology" presented by Eric R. Marsh at an annual meeting of the American Society for Precision Engineering, accessed from the internet site http://www.scribd.com/doc/132020851/Spindle-Tutorial on 2 May 2013, the contents which are herein incorporated by reference. Prior art FIGS. 16A, 16B, 16C and 17 are adapted from this paper.

Figure 16A:
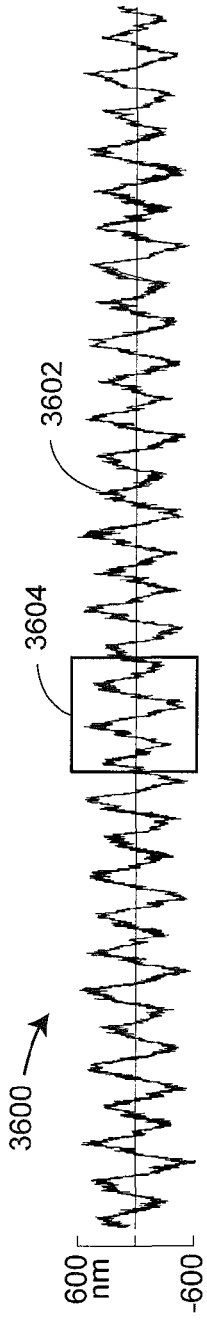
FIGS. 16A-16C are plots of data obtained from a measurement of bearing errors in a lathe spindle.

FIG. 16A is a plot 3600 of data 3602 obtained from a measurement of bearing errors in a lathe spindle. The plot shows data obtained from a single capacitive sensor in an arrangement similar to that of FIGS. 15A and 15B but with a single sphere rather than five spheres. The maximum values observed in the 32 turns of the shaft are seen to be to lie generally within the range of +/−600 nm. An observation that can be immediately made from the plot is that the measured values are different for each of the 32 turns of the shaft.

Figure 16B:
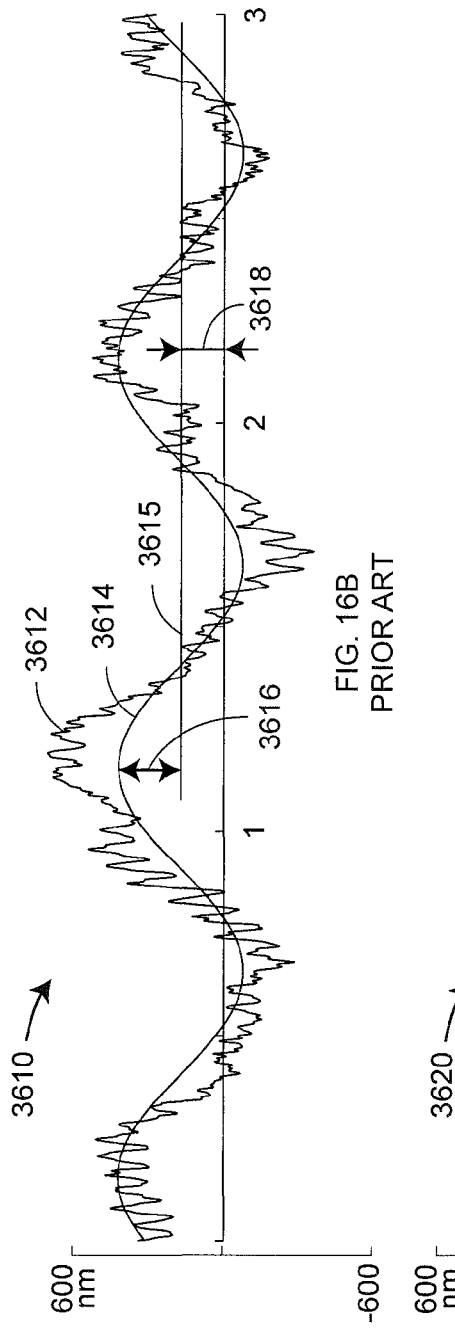
Figure 16C:
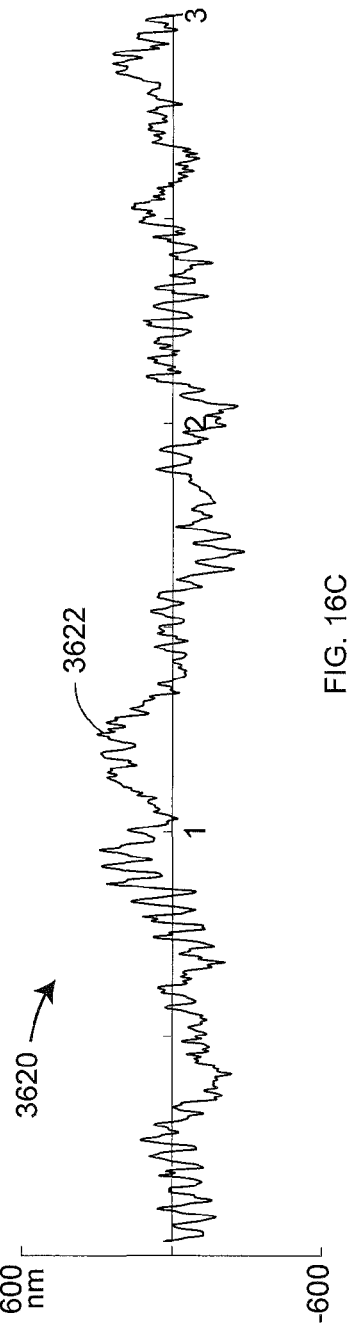

FIG. 16B is a plot 3610 of data 3612 for three cycles within the box 3604 in FIG. 16A. A sinusoidal curve 3614 is fit to the data 3612 and the average of the sinusoidal curve is extracted as line 3615. The sinusoidal curve results largely from the difficulty in perfectly centering the first sphere portion 3514 and the second sphere portion 3516 on the axis of rotation. Because it is generally not possible to perfectly center these spheres on the axis of rotation, the fundamental sinusoidal component is removed during processing of collected data. FIG. 16C is a plot 3620 of the bearing error 3622, obtained by subtracting the values of the sinusoid 3614 from the measured data 3612. The subtracting the fundamental sinusoidal component from the collected data is performed only on the capacitive sensors 3544, 3545, 3546, 3547, which measure radial (side-to-side) displacements, and not on capacitive sensor 3548, which measures axial displacement. For axial displacement, the fundamental sinusoidal variation is meaningful and is not subtracted from the collected data.

Figure 17:
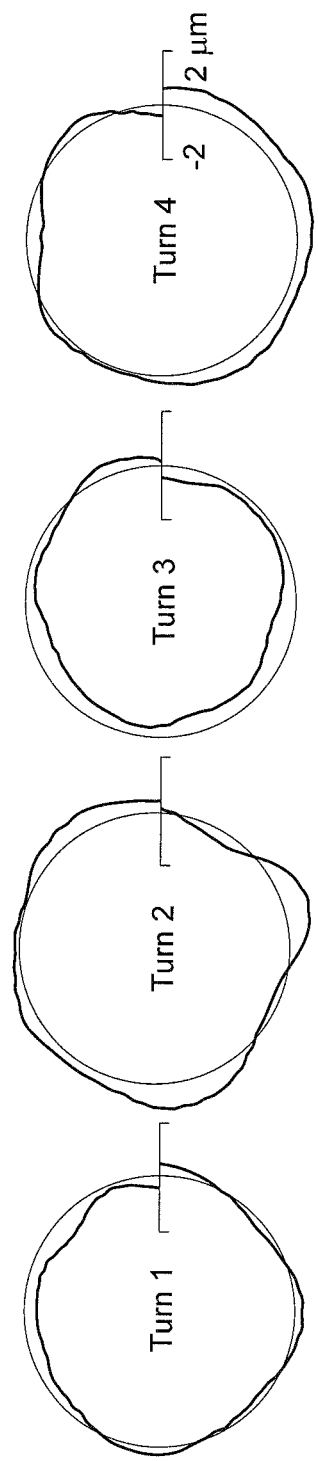
FIG. 17 shows four consecutive rotations of a spindle that contains two bearings.

In general, bearings do not return to their initial displacement after a rotation of 360 degrees. This effect is illustrated in FIG. 17, which shows four consecutive rotations of a spindle that contains two bearings. Turn one begins in the rightmost direction at 0 degrees with an error of between 0 and −1 micrometers. It rotates counterclockwise and after 360 degrees has an error of between 0 and +1 micrometer. The error at an angle of zero degrees for the second turn is the same as the error at 360 degrees for the first turn. By studying the four turns, it can be seen that no two of the turns has the same errors. These results dispel an often held notion that bearing error patterns repeat every 720 degrees.

Figure 18:
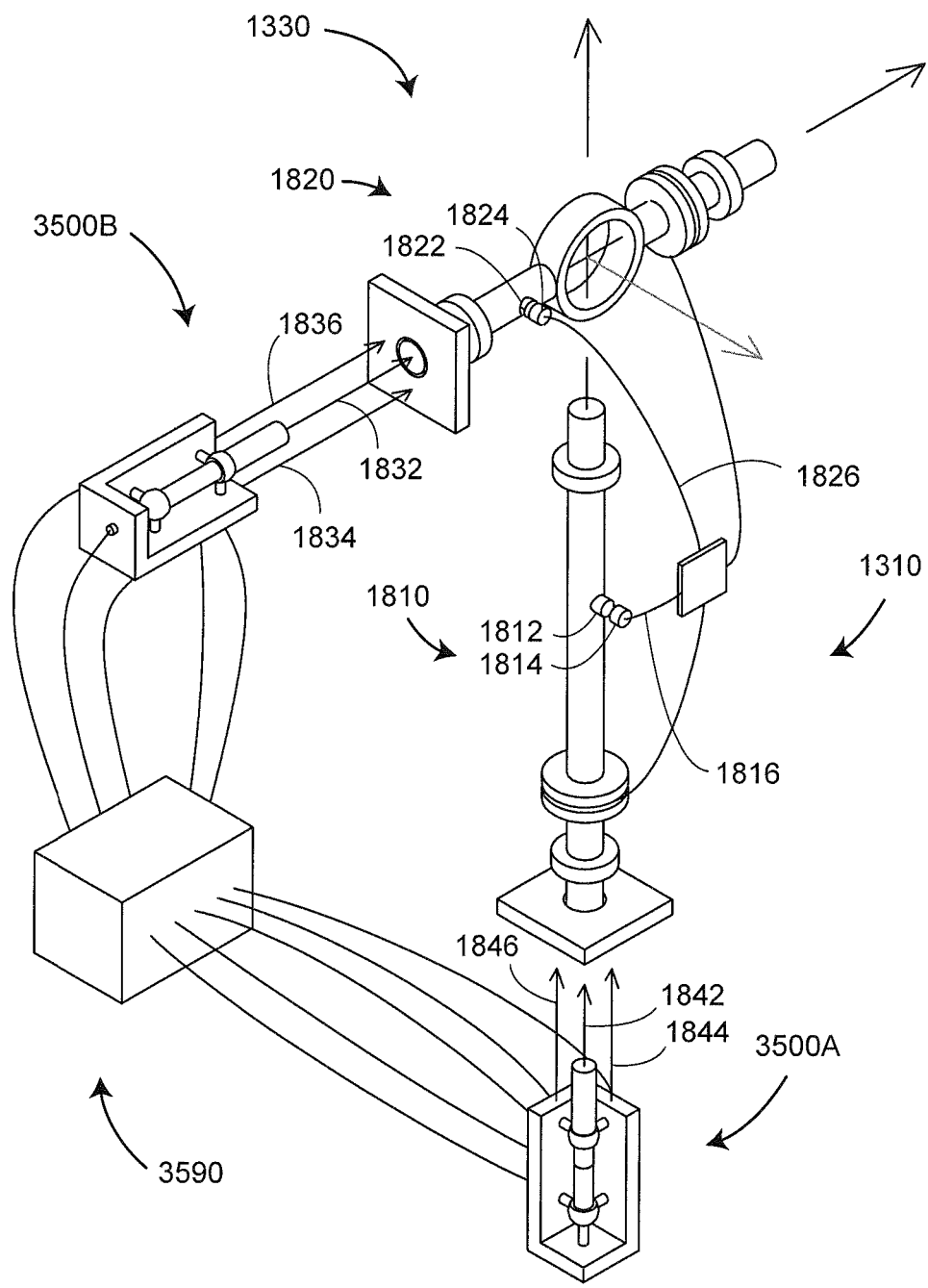
FIG. 18 is a perspective, partially exploded view of laser tracker components and bearing runout measurement apparatus according to an embodiment of the present invention.

FIG. 18 is a perspective view of selected laser tracker components arranged to accept bearing measurement apparatuses 3500A and 3500B, as described hereinabove with reference to FIGS. 15A and 15B. The bearing measurement apparatuses 3500A, 3500B are attached to an electrical circuit 3590. The apparatus 3500A is configured to attach to an azimuth/base assembly 1310. The first shaft portion 3512 shown in FIG. 15A is configured to attach to azimuth axle 1312 shown in FIG. 13. The arrow 1842 indicates an attachment location. An adaptor element (not shown) may be added to join the first shaft portion 3512 to the azimuth axle 1312. The frame 3542 is joined to the base frame 1318 as indicated by the arrows 1844, 1846.

The apparatus 3500B may be a separate bearing measurement apparatus, or it may be the apparatus 3500A attached at a different time to perform the bearing measurement. Alternatively, a procedure may be carried out to measure the bearing errors for a single axis rather than for both axes. The arrows 1832, 1834, and 1836 indicate the positions of attachment.

Bearing errors are generally very repeatable over any 360 degree interval. However, there may be significant variations over different 360 degree intervals. To substantially eliminate bearing errors, it is helpful to limit the range of rotation of the axles 1312, 1332A, 1332B to those angular regions for which bearing calibration data has been taken and to keep track of the rotation angle of the axles during operation of the tracker. Keeping track of current 360 degree rotation interval should be performed even when tracker power is off. In an embodiment, this is done by associating a non-volatile rotation monitor with each axis. An azimuth rotation monitor 1810 includes an azimuth axle attachment 1812 and a fixed frame sensor 1814. Each time the sensor passes the attachment, it produces a signal that indicates the direction of movement. An electrical counter keeps track of the number of revolutions. Many different physical quantities may be measured by the sensors 1814—for example, capacitance, inductance, magnetism, and light. If the rotation is outside the range over which bearing calibration data has been taken, a warning message may be given to the user. A zenith rotation monitor 1820 includes a zenith axle attachment 1822 and a yoke frame sensor 1824. It operators in a manner analogous to the azimuth rotation monitor. Electrical signals from the sensors are sent over connections 1816, 1826 to the circuit board 1325 for processing. The circuit board 1325 may contain a battery to provide non-volatile operation of the monitors.

Other devices may be used to keep track of the current 360 range of the axles. For example, springs may be used to provide a measurable amount of tension correlated to the number of rotations of each axle. It is also possible to use stops to control the amount of rotation to a limited range.

Some angle measuring devices such as angular encoders are designed to measure between 0 and 360 degrees. To keep track of the overall rotation angle, it is customary to speak of unwrapped angles. For example, an angle that drops between 0 degrees, say to −10 degrees, has a wrapped angular reading (for example, by an angular encoder) of 350 degrees but an unwrapped value of −10 degrees. Similarly an angle that exceeds 360 degrees by 10 degrees would have a wrapped angular reading of 10 degrees and an unwrapped value of 370 degrees.

A rotation monitor such as 1810 is a bidirectional counter, which means that it keeps track of the number of forward counts and reverse counts. An axle that completes five rotations in a forward direction and two rotations in a reverse direction has completed 5−2=3 rotations in a forward direction. The (net) number of rotations may be combined with the angle between 0 and 360 degrees measured by an angle measuring device such as an angular encoder to obtain an unwrapped angle: unwrapped angle=wrapped angle+(net rotations)(360), where it is understood that net rotations may be positive or negative.

Figure 19:
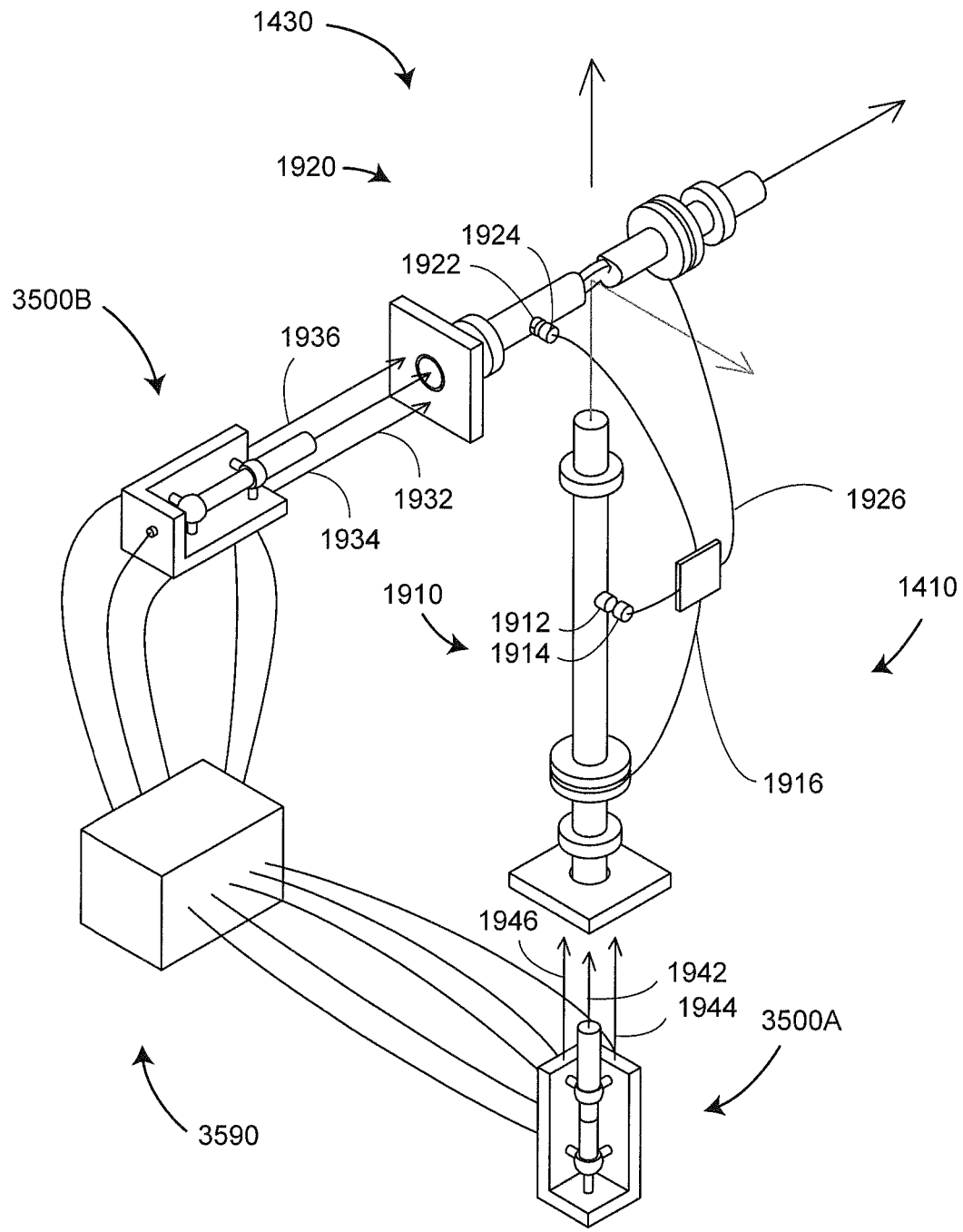
FIG. 19 is a perspective, partially exploded view of laser tracker components and bearing runout measurement apparatus according to an embodiment of the present invention.

FIG. 19 is a perspective view of selected laser tracker components arranged to accept bearing measurement apparatuses 3500A and 3500B, as described hereinabove with reference to FIGS. 15A and 15B. The bearing measurement apparatuses 3500A, 3500B are attached to an electrical circuit 3590. The apparatus 3500A is configured to attach to an azimuth/base assembly 1410. The first shaft portion 3512 shown in FIG. 15A is configured to attach to azimuth axle 1412 shown in FIG. 14. The arrow 1942 indicates an attachment location. An adaptor element (not shown) may be added to join the first shaft portion 3512 to the azimuth axle 1412. The frame 3542 is joined to the base frame 1418 as indicated by the arrows 1944, 1946.

The apparatus 3500B may be a separate bearing measurement apparatus, or it may be the apparatus 3500A attached at a different time to perform the bearing measurement. Alternatively, a procedure may be carried out to measure the bearing errors for a single axis rather than for both axes. The arrows 1932, 1934, and 1936 indicate the positions of attachment.

Bearing errors are generally very repeatable over any 360 degree interval. However, there may be significant variations over different 360 degree intervals. To more completely eliminate bearing errors, it is helpful to limit the range of rotation of the axles 1412, 1432A, 1432B to those angular regions for which bearing calibration data has been taken and to keep track of the rotation angle of the axles during operation of the tracker. Keeping track of the current 360 degree rotation interval should be done even when tracker power is turned off. In an embodiment, this is done by associating a non-volatile rotation monitor with each axis. An azimuth rotation monitor 1910 includes an azimuth axle attachment 1912 and a fixed frame sensor 1914. Each time the sensor passes the attachment, it produces a signal that indicates the direction of movement. An electrical counter keeps track of the number of revolutions. Many different physical quantities may be measured by the sensors 1914—for example, capacitance, inductance, magnetism, and light. If the rotation is outside the range over which bearing calibration data has been taken, a warning message may be given to the user. A zenith rotation monitor 1920 includes a zenith axle attachment 1922 and a yoke frame sensor 1924. It operators in a manner analogous to the azimuth rotation monitor. Electrical signals from the sensors are sent over connections 1916, 1926 to the circuit board 1425 for processing. The circuit board 1425 may contain a battery to provide non-volatile operation of the monitors.

Other devices may be used to keep track of the current 360 range of the axles. For example, springs may be used to provide a measurable amount of tension correlated to the number of rotations of each axle. It is also possible to use stops to control the amount of rotation to a limited range.

In an embodiment, the azimuth axis and zenith axis are rotated by motors within the laser tracker. For example, the motors might be an azimuth motor including rotor 2126 and stator 2127 and a zenith motor including rotor 2156 and stator 2157 as shown in FIGS. 9 and 10. In an embodiment, the angles of rotation are determined by angular encoders, for example, azimuth angular encoder 1316, 1416 and zenith angular encoder 1336, 1436 shown in FIGS. 13 and 14. In an embodiment, data is recorded for each of the read heads in each of the angular encoders. As discussed hereinabove, the bearing measurements may be performed for the azimuth and zenith axes simultaneously or sequentially. In some cases, the data may be raw read-head data that can be post-processed. At the same time, data is collected by the one or more bearing measurement systems.

The bearing errors may be stored as maps or as equations that can be used to reproduce the error values. To avoid confusion, the terms bearing errors are hereinbelow referred to as runout errors. This may help eliminate confusion with errors associated with the individual bearings, which in general are not known from the measurement collected using the methods described hereinabove. It should be understood that the term runout as used herein refers to the general category of errors produced by bearings and not to "total indicated runout" which is a specific term used to represent the total range of error values that may be observed. The collected runout values may be used by a processor contained within the tracker or by an external computer. Essentially any of the processing elements shown in FIG. 11 can be used in computations involving bearing runout.

There are two main ways that the bearing runout may be used: first, to correct the frame of reference of the laser tracker, thereby improving the accuracy of tracker measurements; second, to improve the accuracy of the angular encoder readings. To understand the first of these uses of bearing runout, consider what can happen to a beam of light from the tracker when the azimuth bearings are imperfect. Suppose that the lower bearing is perfectly round and has no bearing error. Suppose that the upper bearing has a maximum runout error of 2 micrometers so that when the light beam from the tracker is pointed to an azimuth angle of zero degrees (in the tracker frame of reference), the azimuth axle is tilted 2 micrometer farther forward than when the azimuth angle is tilted by 180 degrees. Further suppose that the distance between the bearings on the azimuth axis is 0.5 meter. This means that the amount of tilt of the axis with the beam pointed in the forward direction compared to the amount of tilt with the beam pointed in the backward direction is 2 micrometers/0.5 meter=4 microradians. A common method of evaluating the angular accuracy of laser trackers is to perform a procedure called a two-face test. A two-face test is performed by first pointing the laser tracker at a retroreflector located in a particular direction in a frontsight mode. The frontsight mode is by definition the normal mode of operation of the tracker. Next the tracker is put into a backsight mode by first rotating the azimuth of the tracker by 180 degrees and then adjusting the zenith angle of the tracker to point back at the target. The difference in the transverse (side-to-side) coordinates of the retroreflector is a distance that reflects an error in the tracker measurement. This error is referred to as a two-face error. The two-face error is considered a sensitive measurement of tracker error. Suppose that the zenith bearings and angle measuring system are perfect in this instance. Further suppose that the measurement is being made at a distance of 6 meters. The two-face error is this instance 6 meters×4 microradians=24 micrometers. If the bearing runout had been corrected, this 24 micrometer error would have been substantially eliminated. Notice in this case that the error was seen in the vertical direction, which is ordinarily associated with zenith movement of the laser beam. In other words, an error that might on the surface seem to be caused by an error in a measurement of a zenith encoder could instead be caused by errors in the azimuth bearings.

As another example of a similar effect, consider the case in which there is an error in the bearings on the zenith axis. Consider the case in which in frontsight mode the light beam is pointed upward at a zenith angle of 45 degrees with azimuth angle of zero degrees. Then in the backsight mode, the azimuth angle is rotated to 180 degrees and the zenith angle is rotated to −45 degrees. Suppose that there is a runout error in the zenith bearings such that, in frontsight mode, the left bearing pushes the axle upward at a zenith angle of +45 degrees. The axle will point down to the right, and the laser beam will point to the right (assuming the azimuth bearings are perfect). In backsight mode, the bearing will rotate by 180 degrees in the azimuth angle and then reverse the zenith angle. The axle will be pointed down to the left, and the light beam from the tracker will point to the left. The two-face error in this case is largely along the horizontal direction. As in the previous case, this error might be incorrectly assumed to be the result of faulty azimuth angular encoders.

There are several mathematical methods that can be used to correct for the errors caused by the tilting of the beam of beam of light as a result of tilting of the azimuth and zenith axles. It is understood that any such methods may be used as is well known to those of ordinary skill in the art. One method that can be used to is first account for the angle of tilt of the azimuth axis. Equations (1) and (2) may be used. There are three coordinates, x, y, and z, that are used to account for bearing runout in the zenith and azimuth axes. For example, the coordinates used to account for bearing errors in the azimuth axis might be in the x and z directions in a frame of reference that rotates with the azimuth axis. The coordinates used to account for bearing runout in the zenith axis might be in the y and z directions in a frame of reference that rotates with the yoke (azimuth carriage) axis. Given the bearing errors, rotation matrices may be used to determine the overall tilt of the beam of light 1360, 1461 for particular azimuth and zenith angles, where the tilt is taken relative to an ideal beam in which the bearing errors are zero. The amount of offset of the beam of light as a result of bearing runout can be calculated by using standard 4×4 transformation matrices that account for the effects of both rotation and translation as is well known in the art. The azimuth and zenith transformation matrices can be multiplied to obtain a system transformation matrix. Further calculations can be performed to account for effects such as axis offset, axis non-squareness, and other parameters as discussed hereinabove.

A second way that bearing runout data can be used is to correct errors in the readings of angular encoders. Consider first the case in which a perfect encoder disk is placed on an axis and a perfect read-head assembly is placed on a frame that is fixed relative to the disk rotation. If there is no bearing runout, the angular encoder readings will be perfect. Next suppose that there is some bearing runout. In this case, the encoder disk will move relative to the read head. In a system read-head assembly having a single read head, errors will be observed whenever the encoder disk shifts in the direction perpendicular to the lines at the location of the read head. If a plurality of read heads is placed symmetrically about the axis of rotation, the errors caused by the disk movement are reduced but not generally eliminated. By knowing the bearing runout values, a correction can be made to the encoder readings to account for these.

If the axles are allowed to rotate to any angles (not constrained to particular 360 degree regions), only the synchronous portion of the bearing runout can be corrected. In many cases, the asynchronous runout is larger than the synchronous runout—in some cases much larger—and so it is advisable to determine which the 360-degree region of rotation for the azimuth and zenith axis.

There are several applications for which the invention described herein is beneficial. In a first application, the tracker is used to make higher accuracy three-dimensional measurements than would otherwise be possible. These measurements are based on the readings of both a distance meter (ADM or interferometer) and two angular encoders. In a second application, the tracker is used to make distance measurements only in a method called sequential multilateration. Ranging measurements are made with the tracker placed in at least three locations, and preferably four locations. The removal of bearing runout enables measurement high measurement accuracies. The results are used to determine three-dimensional coordinates of a retroreflector target to better accuracies than would be possible by including angular encoder readings. A related method is simultaneous multilateration in which multiple measurements are made simultaneously to a wide-angle retroreflector from three or more laser trackers. Another potential benefit of compensation of bearing runout is to enable the use of relatively less expensive bearings since the resulting accuracy of the bearings is improved by the bearing compensation procedure.

Although the discussion hereinabove has mostly emphasized the importance of correcting bearing runout for the case of multilateration measurements, in many cases, correction to angular measurements may be more important. Properly compensated angular encoders in laser trackers today often provide errors of less than one arc second in measuring the angular rotation of zenith and azimuth axles. In many cases, the bearings may contribute more to a measurement of three-dimensional coordinates of a retroreflector target than the angular encoders. Determining the angular motions of the angular encoders as a function of angular rotation (which may exceed 360 degrees) for both axles may provide a way of significantly improving the angular accuracy of laser trackers. In other words, the data collected in the procedures described above may be used in a kinematic model of the tracker to improve the following four measured values: the two angles (for example, vertical and horizontal angles) to the retroreflector, the distance to the retroreflector, and the position of the tracker origin (the apparent gimbal point).

While the invention has been described with reference to example embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for correcting errors in measurement of three-dimensional coordinates of a retroreflector target by a coordinate measurement device, the coordinate measurement device configured to send a first beam of light to the retroreflector target, the retroreflector target configured to return a portion of the first beam as a second beam, the method comprising steps of:
providing the coordinate measurement device with a first axle, a second axle, a first motor, a second motor, a first angle measuring device, a second angle measuring device, a distance meter, a processor and a memory, the first axle configured to rotate about a first axis, the first axle supported by a first bearing and a second bearing, the first motor configured to rotate the first axle about the first axis by a first angle from among a plurality of first angles, the first angle measuring device configured to measure the first angle, the second axle configured to rotate about a second axis, the second axle supported by a third bearing and a fourth bearing, the second motor configured to rotate the second axle about the second axis by a second angle from among a plurality of second angles, the second angle measuring device configured to measure the second angle, the distance meter configured to measure a first distance from the coordinate measurement device to the retroreflector target based at least in part on a first portion of the second beam received by a first optical detector;
measuring a plurality of first angles with the first angle measuring device;
measuring a plurality of first displacements, each of the plurality of first displacements associated with one of the plurality of first angles, each of the plurality of first displacements taken along one of a plurality of first lines perpendicular to the first axis and passing through a first position on the first axis;
measuring a plurality of second displacements, each of the plurality of second displacements associated with one of the plurality of first angles, each of the plurality of second displacements taken along one of a plurality of second lines perpendicular to the first axis and passing through a second position on the first axis, there being a first separation distance between the first position and the second position;
determining compensation values based at least in part on the plurality of first angles, the plurality of first displacements, the plurality of second displacements, and the first separation distance;
storing the compensation values in the memory;
sending the first beam to the retroreflector target;
measuring a first retroreflector angle with the first angle measuring device;
measuring a second retroreflector angle with the second angle measuring device;
measuring the first distance with the distance meter;
calculating with the processor three-dimensional coordinates of the retroreflector target based at least in part on the first retroreflector angle, the second retroreflector angle, the first distance, and the compensation values; and
storing the three-dimensional coordinates of the retroreflector target in the memory.

2. The method of claim 1 further comprising steps of:
measuring a plurality of third displacements, each of the plurality of third displacements associated with one of the plurality of first angles, each of the plurality of third displacements taken along one of a plurality of third lines perpendicular to the first axis and passing through a third position on the first axis;
measuring a plurality of fourth displacements, each of the plurality of fourth displacements associated with one of the plurality of first angles, each of the plurality of fourth displacements taken along one of a plurality of fourth lines perpendicular to the first axis and passing through a fourth position on the first axis, there being a second separation distance between the third position and the fourth position; and
in the step of determining compensation values, the compensation values are further based at least in part on the plurality of third displacements and the plurality of fourth displacements.

3. The method of claim 2 further including steps of:
measuring a plurality of second angles with the second angle measuring device;
measuring a plurality of fifth displacements, each of the plurality of fifth displacements associated with one of the plurality of second angles, each of the plurality of fifth displacements taken along one of a plurality of fifth lines perpendicular to the second axis and passing through a fifth position on the second axis;
measuring a plurality of sixth displacements, each of the plurality of sixth displacements associated with one of the plurality of second angles, each of the plurality of sixth displacements taken along one of a plurality of sixth lines perpendicular to the second axis and passing through a sixth position on the second axis, there being a third separation distance between the fifth position and the sixth position;
measuring a plurality of seventh displacements, each of the plurality of seventh displacements associated with one of the plurality of second angles, each of the plurality of seventh displacements taken along one of a plurality of seventh lines perpendicular to the second axis and passing through a seventh position;
measuring a plurality of eighth displacements, each of the plurality of eighth displacements associated with one of the plurality of second angles, each of the plurality of eighth displacements taken along an eighth line perpendicular to the second axis and passing through the eighth position, there being a fourth separation distance between the seventh position and the eighth position; and
in the step of determining compensation values, further determining the compensation values based at least in part on the plurality of second angles, the plurality of fifth displacements, the plurality of sixth displacements, the plurality of seventh displacements, and the plurality of eighth displacements, the third separation distance, and the fourth separation distance.

4. The method of claim 1 wherein in the step of determining compensation values, the compensation values include a plurality of angles of tilt of the first axis, wherein each of the plurality of angles of tilt is associated with one of the first angles from among the plurality of first angles.

5. The method of claim 1 further comprising steps of:
providing a test apparatus configured to be removably attached to the first axle, the test apparatus having a first sensor and a second sensor;
attaching the test apparatus to the first axle so as to place the first sensor along one of the plurality of first lines and to place the second sensor along one of the plurality of second lines; and
wherein, in the step of measuring a plurality of first displacements, the first displacements are measured with the first sensor and, in the step of measuring a plurality of second displacements, the second displacements are measured with the second sensor.

6. The method of claim 5 wherein, in the step of providing a test apparatus, the first sensor and the second sensor are capacitance sensors.

7. The method of claim 6 wherein, in the step of providing a test apparatus, the first sensor is proximate to a first spherical surface and the second sensor is proximate to a second spherical surface.

8. The method of claim 1 further comprising steps of:
providing a first sensor and a second sensor, the first sensor located along one of the plurality of first lines and to place the second sensor along one of the plurality second lines; and
wherein, in the step of measuring a plurality of first displacements, the first displacements are measured with the first sensor and, in the step of measuring a plurality of second displacements, the second displacements are measured with the second sensor.

9. The method of claim 1 wherein, in the step of measuring a plurality of first angles, each of the first angles from among the plurality of first angles is unwrapped to provide a plurality of first unwrapped angles, each of the first unwrapped angles varying without cyclic discontinuities.

10. The method of claim 9 wherein the step of determining compensation values further includes calculating a fundamental sinusoidal component.

11. The method of claim 9 wherein:
the method further-includes a step of measuring a number of rotations of the first axle about the first axis; and
the step of determining compensation values further includes determining a bearing error based at least in part on the number of rotations.

12. The method of claim 11 further including steps of:
providing a rotation counter; and
measuring the number of rotations of the first axle with the rotation counter.

13. The method of claim 12 wherein, in the step of measuring the number of rotations, the rotation counter includes a first counter portion and a second counter portion, the first counter portion attached to the first axle, the second counter portion attached to a housing that is stationary with respect to the rotation of the first axle, the first counter portion and the second counter portion configured to produce a signal for each of the rotations of the first axle, the rotation counter further configured to respond to a direction of the rotation of the first axle so as to increase a number of counts for the rotations in a first rotation direction and to decrease the number of counts for the rotations in a direction opposite the first rotation direction.

14. The method of claim 13 wherein, in the step of measuring the number of rotations, the rotation counter is configured to measure the number of rotations when the first angle measuring device is not operable.

15. The method of claim 13 wherein, in the step of measuring the number of rotations, the rotation counter is powered by a battery.

16. A coordinate measurement device for measuring three-dimensional coordinates of a retroreflector target, the coordinate measurement device configured to send a first beam of light to the retroreflector target, the retroreflector target configured to return a portion of the first beam as a second beam, the device comprising:
a first axle, a second axle, a first motor, a second motor, a first angle measuring device, a second angle measuring device, a distance meter, a rotation counter, a processor and a memory, the first axle configured to rotate about a first axis, the first axle supported by a first bearing and a second bearing, the first motor configured to rotate the first axle about the first axis by a first angle, the first angle measuring device configured to measure the first angle, the second axle configured to rotate about a second axis, the second axle supported by a third bearing and a fourth bearing, the second motor configured to rotate the second axle about the second axis by a second angle, the second angle measuring device configured to measure the second angle, the distance meter configured to measure a first distance from the coordinate measurement device to the retroreflector target based at least in part on a first portion of the second beam received by a first optical detector, the rotation counter configured to measure a number of rotations of the first axle, the rotation counter further configured to keep track of a current 360 degree rotation interval even when a device power is off;
wherein the processor is configured to determine three dimensional coordinates based at least in part on the first distance, the first angle, the second angle, the 360 degree rotation interval and compensation values, the compensation values being associated with the first bearing, the second bearing, the third bearing and the fourth bearing, the compensation values further being a function of at least the 360 degree rotation interval.

* * * * *